United States Patent
Albrandt et al.

(10) Patent No.: US 6,602,694 B1
(45) Date of Patent: Aug. 5, 2003

(54) UNCOUPLING PROTEIN 4 (UCP-4)

(75) Inventors: Keith Albrandt, San Diego, CA (US); Kevin Beaumont, San Diego, CA (US); Andrew A. Young, San Diego, CA (US)

(73) Assignee: Amylin Pharmaceuticals, Inc, San Diego, CA (US)

( * ) Notice: Subject to any disclaimer, the term of this patent is extended or adjusted under 35 U.S.C. 154(b) by 0 days.

(21) Appl. No.: 09/743,847

(22) PCT Filed: Jul. 13, 1999

(86) PCT No.: PCT/US99/15861

§ 371 (c)(1),
(2), (4) Date: Jun. 27, 2001

(87) PCT Pub. No.: WO00/04037

PCT Pub. Date: Jan. 27, 2000

Related U.S. Application Data

(60) Provisional application No. 60/092,737, filed on Jul. 14, 1998.

(51) Int. Cl.[7] .............................. C12N 9/00; C07K 14/00
(52) U.S. Cl. ........................ 435/183; 530/350; 530/333
(58) Field of Search ................. 530/350, 333; 536/23.1, 23.5; 435/69.1, 70.1, 325, 455, 183

(56) References Cited

U.S. PATENT DOCUMENTS 5,741,666 A   4/1998   Tartaglia

FOREIGN PATENT DOCUMENTS

WO   WO 96/31526   10/1996

OTHER PUBLICATIONS

Sanchis et al. BMCP1, a novel mitochondrial carrier with high expression in the central nervous system of human and rodents and respiration uncoupling activity in recombinant yeast. J. Biol. Chem. 273:34611–34615, 1998.*

Mao et al. UCP4, a novel brain–specific mitochondrial protein that reduces membrane potential in mammalian cells. FEBS Letters 443:326–330, 1999.*

Apoorva Mandavilli, Protein folds shield different Roles, BioMednet News, Nov. 1, 2001.*

Peer Bork and Eugene V. Koonin, Predicting functions from protein sequences—where are the bottlenecks? Nature Genetics 18:313–318, 1998.*

Bairoch, A., et al, "The PROSITE database, its status in 1997," Nucleic Acids Research, 25(1):217–221 (1997).

Bathgate, B., et al., "Functional expression of the rat brown adipose tissue uncoupling protein in Saccharomyces cerevisiae," Molecular Microbiology, 6(3):363–370 (1992).

Bianco, A.C., et al, "Triiodothyronine Amplifies Norepinephrine Stimulation of Uncoupling Protein Gene Transcription by a Mechanism Not Requiring Protein Synthesis," Journal of Biological Chemistry, 263(34):18168–18175 (1988).

Boss, O., et al, "Uncoupling protein–3: a new member of the mitochondrial carrier family with tissue–specific expression," FEBS Letters, 408:39–42 (1997).

Bouillaud, F., et al, "A sequence related to a DNA recognition element is essential for the inhibition by nucleotides of proton transport through the mitochondrial uncoupling protein," EMBO Journal, 13(8):1990–1997 (1994).

Ferguson, M.A.J., et al. "Cell–Surface Anchoring of Proteins Via Glycosylphosphatidylinositol Structures", Annu. Rev. Biochem. 57:285–320 (1988).

Fleury, C., et al, "Uncoupling protein–2: a novel gene linked to obesity and hyperinsulinemia," Nature Genetics 15:269–272 (1997).

Garlid, K.D., et al, "On the Mechanism of Fatty Acid–induced Proton Transport by Mitochondrial Uncoupling Protein," Journal of Biological Chemistry, 271(5):2615–2620 (1996).

Goeddel, D.V., et al, "Synthesis of human fibroblast interferon by E. coli," Nucleic Acids Research, 8(18):4057–4075 (1980).

Gonzalez–Barroso, M.M., et al, "Activation of the uncoupling protein by fatty acids is modulated by mutations in the C–terminal region of the protein," Eur J Biochem 239:445–450 (1996).

Kane, J.F., "Effects of rare codon clusters on high–level expression of heterologous proteins in Escherichia coli," Current Opinion in Biotechnology, 6:494–500 (1995).

Klingenberg, M., "Mechanism and evolution of the uncoupling protein of brown adipose tissue," Trends Biochem. Sci., 15:108–112 (1990).

Knopfel, T., et al, "Metabotropic Glutamate Receptors: Novel Targets for Drug Development," J Medicinal Chemistry, 38(9):1417–1426 (1995).

Kopecky, J., et al, "Expression of the Mitochondrial Uncoupling Protein Gene from the aP2 Gene Promoter Prevents Genetic Obesity," J Clinical Investigation, 96:2914–2923 (1995).

(List continued on next page.)

Primary Examiner—Yvonne Eyler
Assistant Examiner—Ruixiang Li

(57) ABSTRACT

A novel uncoupling protein, which we have designated UCP-4, that is expressed in various tissues, including brain, heart, pancreas, and muscle tissue, and nucleic acid molecules which encode for said novel protein, are described. Methods of screening for compounds that regulate the expression and the activity of UCP-4 are described, as well as methods of treating diseases or conditions in which the regulation of thermogenesis or respiratory ATP synthesis is desired. Such conditions include obesity, diabetes, malignant hyperthermia, and fever. The construction of cell lines that express UCP-4 is also described.

5 Claims, 5 Drawing Sheets

OTHER PUBLICATIONS

Larkin, S., et al, "Regulation of the Third Member of the Uncoupling Protein Family, UCP3, by Cold and Thyroid Hormone," *Biochem Biophys Res Comm,* 240:222–227 (1997).

Leibel, R.L., et al, "Changes in Energy Expenditure Resulting from Altered Body Weight," *New England Journal of Medicine* 332(10):621–628 (1995).

Lennon, G., et al, "The I.M.A.G.E. Consortium: An Integrated Molecular Analysis of Genomes and Their Expression," *Genomics,* 33:151–152 (1996).

Lowell, B.B., "Development of obesity in transfenic mice after genetic ablation of brown adipose tissue," *Nature* 366:740–742 (1993).

MacLennan, D.H., et al, "Discordance between phenotype and genotype inmalignant hyperthermia," *Curr. Opin. Neurol.,* 8:397–401 (1995).

Mickelson, J.R., et al., "Malignant Hyperthermia: Excitation–Contraction Coupling, $CA^{2+}$ Release Channel, and Cell $CA^{2+}$ Regulation Defects," *Physiol. Rev.,* 76:537–92 (1996).

Miller, D.A., "Human gene therapy comes of age," *Nature* 357(6378): 455–460 (1992).

Mumberg, D., et al, "Regulatable promoters of *Saccharomyces cerevisiae:* comparison of transcriptional activity and their use for heterologous expression," *Nucleic Acids Research,* 22(25):5767–5768 (1994).

Murdza–Inglis, D.L., et al, "Functional Reconsitution of Rat Uncoupling Protein Following Its High Level Expression in Yeast," *J Biol Chem,* 260(18):11871–11875 (1991).

Murdza–Inglis, D.L., et al, "A Single Mutation in Uncoupling Protein of Rat Brown Adipose Tissue Mitochondria Abolishes GDP Sensitivity of H Transport," *J Biol Chem* 269(10):7435–7438 (1994).

Nicholls, D.G., et al, "Thermogenic Mechanisms in Brown Fat," *Physiological Reviews,* 64:2–40 (1984).

Rehnmark, S., et al, "α– and β–Adrenergic Induction of the Expression of the Uncoupling Protein Thermogenin in Brown Adipocytes Differentiated in Culture," *J Biol Chem,* 265(27):16464–16471 (1990).

Ricquier, D., et al, "Expression of Uncoupling Protein mRNA in Thermogenic or Weakly Thermogenic Brown Adipose Tissue," *J Biol Chem,* 261(30):13905–13910 (1996).

Rothwell, N.J., et al, "A role for brown adipose tissue in diet–induced thermogenesis," *Nature* 281:31–35 (1979).

Steinfath, et al., Anasthesiol. Intensivmed Notfallmed Schmerzther, 31:334–43 (1996) [English abstract only] Article in German.

* cited by examiner

```
                                      GAGCAGCACCAGAAAAGTACCACTGTAAGTCATGAG    36

ATG TCT GGT CTG AAT TGG AAA CCC TTT GTA TAT GGC GGC CTT GCC TCT ATC GTG GCT    93
 M   S   G   L   N   W   K   P   F   V   Y   G   G   L   A   S   I   V   A

GAG TTT GGG ACT TTC CCT GTG GAC CTT ACC AAA ACA CGA CTT CAG GTT CAA GGC CAA   150
 E   F   G   T   F   P   V   D   L   T   K   T   R   L   Q   V   Q   G   Q

AGC ATT GAT GCC CGT TTC AAA GAG ATA AAA TAT AGA GGG ATG TTC CAT GCG CTG TTT   207
 S   I   D   A   R   F   K   E   I   K   Y   R   G   M   F   H   A   L   F

CGC ATC TGT AAA GAG GAA GGT GTA TTG GCT CTC TAT TCA GGA ATT GCT CCT GCG TTG   264
 R   I   C   K   E   E   G   V   L   A   L   Y   S   G   I   A   P   A   L

CTA AGA CAA GCA TCA TAT GGC ACC ATT AAA ATT GGG ATT TAC CAA AGC TTG AAG CGC   321
 L   R   Q   A   S   Y   G   T   I   K   I   G   I   Y   Q   S   L   K   R

TTA TTC GTA GAA CGT TTR GAA GAT GAA ACT CTT TTA ATT AAT ATG ATC TGT GGG GTA   378
 L   F   V   E   R   L   E   D   E   T   L   L   I   N   M   I   C   G   V

GTG TCA GGA GTG ATA TCT TCC ACT ATA GCC AAT CCC ACC GAT GTT CTA AAG ATT CGA   435
 V   S   G   V   I   S   S   T   I   A   N   P   T   D   V   L   K   I   R

ATG CAR GCT CAA GGA AGC TTG TTC CAA GGG AGC ATG ATT GGA AGC TTT ATC GAT ATA   492
 M   Q   A   Q   G   S   L   F   Q   G   S   M   I   G   S   F   I   D   I

TAC CAA CAA GAA GGC ACC AGG GGT CTG TGG AGG GGT GTG GTT CCA ACT GCT CAG CGT   549
 Y   Q   Q   E   G   T   R   G   L   W   R   G   V   V   P   T   A   Q   R

GCT GCC ATC GTT GTA GGA GTA GAG CTA CCA GTC TAT GAT ATT ACT AAG AAG CAT TTA   606
 A   A   I   V   V   G   V   E   L   P   V   Y   D   I   T   K   K   H   L

ATA TTG TCA GGA ATG ATG GGC GAT ACA ATT TTA ACT CAC TTC GTT TCC AGC TTT ACA   663
 I   L   S   G   M   M   G   D   T   I   L   T   H   F   V   S   S   F   T

TGT GGT TTG GCT GGG GCT CTG GCC TCC AAC CCG GTT GAT GTG GTT CGA ACT CGC ATG   720
 C   G   L   A   G   A   L   A   S   N   P   V   D   V   V   R   T   R   M

ATG AAC CAG AGG GCA ATC GTG GGA CAT GTG GAT CTC TAT AAG GGC ACT GTT GAT GGT   777
 M   N   Q   R   A   I   V   G   H   V   D   L   Y   K   G   T   V   D   G

ATT TTA AAG ATG TGG AAA CAT GAG GGC TTT TTT GCA CTC TAT AAA GGA TTT TGG CCA   834
 I   L   K   M   W   K   H   E   G   F   F   A   L   Y   K   G   F   W   P
                                     ___ ___ ___ ___ ___ ___ ___ ___ ___

AAC TGG CTT CGG CTT GGA CCC TGG AAC ATC ATT TTT TTT ATT ACA TAC GAG CAG CTA   891
 N   W   L   R   L   G   P   W   N   I   I   F   F   I   T   Y   E   Q   L
___ ___ ___ ___ ___ ___ ___ ___ ___

AAG AGG CTT CAA ATC TAA GAACTGAATTATATGTGAGCCCAGCCC                            936
 K   R   L   Q   I   *
```

|   | 1 | 2 | 3 | 4 | 5 | 6 |
|---|---|---|---|---|---|---|
| A | left atrium | frontal lobe | parotid | throat | kidney | thyroid |
| B | right atrium | temporal lobe | esophagus | trachea bronchial | bladder | pancreas |
| C | left ventricle | occipital lobe | stomach | left lung | prostate | adrenal |
| D | right ventricle | parietal lobe | small intestine | right lung | testis | tonsil |
| E | septum interventricle | thalamus | colon | diaphragm | uterus | thymus |
| F | pericardium | pons | rectum | skeletal muscle | breast | spleen |
| G | human DNA | cerebellum | liver | tongue | ovary | lymph node |
| H | plasmid DNA | spinal cord | gallbladder | adipose tissue | placenta | appendix |

Fig. 4B

SEQUENCE LISTING

<160> NUMBER OF SEQ ID NOS: 5

<210> SEQ ID NO 1
<211> LENGTH: 936
<212> TYPE: DNA
<213> ORGANISM: Homo sapiens

<400> SEQUENCE: 1

```
gagcagcacc agaaaagtac cactgtaagt catgagatgt ctggtctgaa ttggaaaccc      60
tttgtatatg gcggccttgc ctctatcgtg gctgagtttg ggactttccc tgtggacctt     120
accaaaacac gacttcaggt tcaaggccaa agcattgatg cccgtttcaa agagataaaa     180
tatagaggga tgttccatgc gctgtttcgc atctgtaaag aggaaggtgt attggctctc     240
```

-continued

```
tattcaggaa ttgctcctgc gttgctaaga caagcatcat atggcaccat taaaattggg    300
atttaccaaa gcttgaagcg cttattcgta gaacgtttrg aagatgaaac tcttttaatt    360
aatatgatct gtggggtagt gtcaggagtg atatcttcca ctatagccaa tcccaccgat    420
gttctaaaga ttcgaatgca rgctcaagga agcttgttcc aagggagcat gattggaagc    480
tttatcgata tataccaaca agaaggcacc aggggtctgt ggagggtgt ggttccaact     540 gctcagcgtg ctgccatcgt tgtaggagta gagctaccag tctatgatat tactaagaag    600
catttaatat tgtcaggaat gatgggcgat acaattttaa ctcacttcgt ttccagcttt    660
acatgtggtt tggctgggc tctggcctcc aacccggttg atgtggttcg aactcgcatg     720
atgaaccaga gggcaatcgt gggacatgtg gatctctata agggcactgt tgatggtatt    780
ttaaagatgt ggaaacatga gggcttttt gcactctata aaggattttg ccaaactgg     840 cttcggcttg gaccctggaa catcatttt tttattacat acgagcagct aaagaggctt     900
caaatctaag aactgaatta tatgtgagcc cagccc                              936
```

<210> SEQ ID NO 2
<211> LENGTH: 290
<212> TYPE: PRT
<213> ORGANISM: Homo sapiens

<400> SEQUENCE: 2

```
Met Ser Gly Leu Asn Trp Lys Pro Phe Val Tyr Gly Gly Leu Ala Ser
1               5                   10                  15

Ile Val Ala Glu Phe Gly Thr Phe Pro Val Asp Leu Thr Lys Thr Arg
            20                  25                  30

Leu Gln Val Gln Gly Gln Ser Ile Asp Ala Arg Phe Lys Glu Ile Lys
        35                  40                  45

Tyr Arg Gly Met Phe His Ala Leu Phe Arg Ile Cys Lys Glu Glu Gly
    50                  55                  60

Val Leu Ala Leu Tyr Ser Gly Ile Ala Pro Ala Leu Leu Arg Gln Ala
65                  70                  75                  80

Ser Tyr Gly Thr Ile Lys Ile Gly Ile Tyr Gln Ser Leu Lys Arg Leu
                85                  90                  95

Phe Val Glu Arg Leu Glu Asp Glu Thr Leu Leu Ile Asn Met Ile Cys
            100                 105                 110

Gly Val Val Ser Gly Val Ile Ser Ser Thr Ile Ala Asn Pro Thr Asp
        115                 120                 125

Val Leu Lys Ile Arg Met Gln Ala Gln Gly Ser Leu Phe Gln Gly Ser
    130                 135                 140

Met Ile Gly Ser Phe Ile Asp Ile Tyr Gln Gln Glu Gly Thr Arg Gly
145                 150                 155                 160

Leu Trp Arg Gly Val Pro Thr Ala Gln Arg Ala Ala Ile Val Val
                165                 170                 175

Gly Val Glu Leu Pro Val Tyr Asp Ile Thr Lys Lys His Leu Ile Leu
            180                 185                 190

Ser Gly Met Met Gly Asp Thr Ile Leu Thr His Phe Val Ser Ser Phe
        195                 200                 205

Thr Cys Gly Leu Ala Gly Ala Leu Ala Ser Asn Pro Val Asp Val Val
    210                 215                 220

Arg Thr Arg Met Met Asn Gln Arg Ala Ile Val Gly His Val Asp Leu
225                 230                 235                 240

Tyr Lys Gly Thr Val Asp Gly Ile Leu Lys Met Trp Lys His Glu Gly
```

```
                          245                 250                 255
Phe Phe Ala Leu Tyr Lys Gly Phe Trp Pro Asn Trp Leu Arg Leu Gly
                260                 265                 270

Pro Trp Asn Ile Ile Phe Phe Ile Thr Tyr Glu Gln Leu Lys Arg Leu
            275                 280                 285

Gln Ile
    290

<210> SEQ ID NO 3
<211> LENGTH: 307
<212> TYPE: PRT
<213> ORGANISM: Homo sapiens

<400> SEQUENCE: 3

Met Gly Gly Leu Thr Ala Ser Asp Val His Pro Thr Leu Gly Val Gln
1               5                   10                  15

Leu Phe Ser Ala Gly Ile Ala Ala Cys Leu Ala Asp Val Ile Thr Phe
                20                  25                  30

Pro Leu Asp Thr Ala Lys Val Arg Leu Gln Val Gln Gly Glu Cys Pro
            35                  40                  45

Thr Ser Ser Val Ile Arg Tyr Lys Gly Val Leu Gly Thr Ile Thr Ala
        50                  55                  60

Val Val Lys Thr Glu Gly Arg Met Lys Leu Tyr Ser Gly Leu Pro Ala
65                  70                  75                  80

Gly Leu Gln Arg Gln Ile Ser Ser Ala Ser Leu Arg Ile Gly Leu Tyr
                85                  90                  95

Asp Thr Val Gln Glu Phe Leu Thr Ala Gly Lys Glu Thr Ala Pro Ser
            100                 105                 110

Leu Gly Ser Lys Ile Leu Ala Gly Leu Thr Thr Gly Gly Val Ala Val
        115                 120                 125

Phe Ile Gly Gln Pro Thr Glu Val Val Lys Val Arg Leu Gln Ala Gln
130                 135                 140

Ser His Leu His Gly Ile Lys Pro Arg Tyr Thr Gly Thr Tyr Asn Ala
145                 150                 155                 160

Tyr Arg Ile Ile Ala Thr Thr Glu Gly Leu Thr Gly Leu Trp Lys Gly
                165                 170                 175

Thr Thr Pro Asn Leu Met Arg Ser Val Ile Ile Asn Cys Thr Glu Leu
            180                 185                 190

Val Thr Tyr Asp Leu Met Lys Glu Ala Phe Val Lys Asn Asn Ile Leu
        195                 200                 205

Ala Asp Asp Val Pro Cys His Leu Val Ser Ala Leu Ile Ala Gly Phe
210                 215                 220

Cys Ala Thr Ala Met Ser Ser Pro Val Asp Val Val Lys Thr Arg Phe
225                 230                 235                 240

Ile Asn Ser Pro Pro Gly Gln Tyr Lys Ser Val Pro Asn Cys Ala Met
                245                 250                 255

Lys Val Phe Thr Asn Glu Gly Pro Thr Ala Phe Phe Lys Gly Leu Val
            260                 265                 270

Pro Ser Phe Leu Arg Leu Gly Ser Trp Asn Val Ile Met Phe Val Cys
        275                 280                 285

Phe Glu Gln Leu Lys Arg Glu Leu Ser Lys Ser Arg Gln Thr Met Asp
290                 295                 300

Cys Ala Thr
305
```

```
<210> SEQ ID NO 4
<211> LENGTH: 309
<212> TYPE: PRT
<213> ORGANISM: Homo sapiens

<400> SEQUENCE: 4

Met Val Gly Phe Lys Ala Thr Asp Val Pro Thr Ala Thr Val Lys
1               5                   10                  15

Phe Leu Gly Ala Gly Thr Ala Ala Cys Ile Ala Asp Leu Ile Thr Phe
                20                  25                  30

Pro Leu Asp Thr Ala Lys Val Arg Leu Gln Ile Gln Gly Glu Ser Gln
                35                  40                  45

Gly Pro Val Arg Ala Thr Ala Ser Ala Gln Tyr Arg Gly Val Met Gly
    50                  55                  60

Thr Ile Leu Thr Met Val Arg Thr Glu Gly Pro Arg Ser Leu Tyr Asn
65                  70                  75                  80

Gly Leu Val Ala Gly Leu Gln Arg Gln Met Ser Phe Ala Ser Val Arg
                85                  90                  95

Ile Gly Leu Tyr Asp Ser Val Lys Gln Phe Tyr Thr Lys Gly Ser Glu
                100                 105                 110

His Ala Ser Ile Gly Ser Arg Leu Leu Ala Gly Ser Thr Thr Gly Ala
                115                 120                 125

Leu Ala Val Ala Val Ala Gln Pro Thr Asp Val Val Lys Val Arg Phe
130                 135                 140

Gln Ala Gln Ala Arg Ala Gly Gly Gly Arg Arg Tyr Gln Ser Thr Val
145                 150                 155                 160

Asn Ala Tyr Lys Thr Ile Ala Arg Glu Glu Gly Phe Arg Gly Leu Trp
                165                 170                 175

Lys Gly Thr Ser Pro Asn Val Ala Arg Asn Ala Ile Val Asn Cys Ala
                180                 185                 190

Glu Leu Val Thr Tyr Asp Leu Ile Lys Asp Ala Leu Leu Lys Ala Asn
                195                 200                 205

Leu Met Thr Asp Asp Leu Pro Cys His Phe Thr Ser Ala Phe Gly Ala
210                 215                 220

Gly Phe Cys Thr Thr Val Ile Ala Ser Pro Val Asp Val Val Lys Thr
225                 230                 235                 240

Arg Tyr Met Asn Ser Ala Leu Gly Gln Tyr Ser Ser Ala Gly His Cys
                245                 250                 255

Ala Leu Thr Met Leu Gln Lys Glu Gly Pro Arg Ala Phe Tyr Lys Gly
                260                 265                 270

Phe Met Pro Ser Phe Leu Arg Leu Gly Ser Trp Asn Val Val Met Phe
                275                 280                 285

Val Thr Tyr Glu Gln Leu Lys Arg Ala Leu Met Ala Ala Cys Thr Ser
    290                 295                 300

Arg Glu Ala Pro Phe
305

<210> SEQ ID NO 5
<211> LENGTH: 310
<212> TYPE: PRT
<213> ORGANISM: Homo sapiens

<400> SEQUENCE: 5

Met Val Gly Leu Lys Pro Ser Asp Val Pro Thr Met Ala Val Lys
1               5                   10                  15
```

-continued

```
Phe Leu Gly Ala Gly Thr Ala Ala Cys Phe Ala Asp Leu Val Thr Phe
            20                  25                  30

Pro Leu Asp Thr Ala Lys Val Arg Leu Gln Ile Gln Gly Glu Asn Gln
            35                  40                  45

Ala Val Gln Thr Ala Arg Leu Val Gln Tyr Arg Gly Val Leu Gly Thr
 50                  55                  60

Ile Leu Thr Met Val Arg Thr Glu Gly Pro Cys Ser Pro Tyr Asn Gly
 65                  70                  75                  80

Leu Val Ala Gly Leu Gln Arg Gln Met Ser Phe Ala Ser Ile Arg Ile
            85                  90                  95

Gly Leu Tyr Asp Ser Val Lys Gln Val Tyr Thr Pro Lys Gly Ala Asp
            100                 105                 110

Asn Ser Ser Leu Thr Thr Arg Ile Leu Ala Gly Cys Thr Thr Gly Ala
            115                 120                 125

Met Ala Val Thr Cys Ala Gln Pro Thr Asp Val Val Lys Val Arg Phe
 130                 135                 140

Gln Ala Ser Ile His Leu Gly Pro Ser Arg Ser Asp Arg Lys Tyr Ser
145                 150                 155                 160

Gly Thr Met Asp Ala Tyr Arg Thr Ile Ala Arg Glu Glu Gly Val Arg
            165                 170                 175

Gly Leu Trp Lys Gly Thr Leu Pro Asn Ile Met Arg Asn Ala Ile Val
            180                 185                 190

Asn Cys Ala Glu Val Val Thr Tyr Asp Ile Leu Lys Glu Lys Leu Leu
            195                 200                 205

Asp Tyr His Leu Leu Thr Asp Asn Phe Pro Cys His Phe Val Ser Ala
            210                 215                 220

Phe Gly Ala Gly Phe Cys Ala Thr Val Val Ala Ser Pro Val Asp Val
225                 230                 235                 240

Val Lys Thr Arg Tyr Met Asn Ser Pro Pro Gly Gln Tyr Phe Ser Pro
            245                 250                 255

Leu Asp Cys Met Ile Lys Met Val Ala Gln Glu Gly Pro Thr Tyr Lys
            260                 265                 270

Gly Phe Thr Pro Ser Phe Leu Arg Leu Gly Ser Trp Asn Val Val Met
            275                 280                 285

Phe Val Thr Tyr Glu Gln Leu Lys Arg Ala Leu Met Lys Val Gln Met
            290                 295                 300

Leu Arg Glu Ser Pro Phe
305                 310
```

UNCOUPLING PROTEIN 4 (UCP-4)

This application is a 371 of PCT/US99/15861, filed on Jul. 13, 1999, which claims the benefit of U.S. Provisional Application No. 60/092,737, filed Jul. 14, 1998.

FIELD OF THE INVENTION

A novel uncoupling protein, which we have designated UCP-4, that is expressed in various tissues, including brain, heart, pancreas, and muscle tissue, and nucleic acid molecules which encode said novel protein, are described. Methods of screening for compounds that regulate the expression and the activity of UCP-4 are described, as well as methods of treating diseases or conditions in which the regulation of thermogenesis, or respiratory ATP synthesis, is desired. Such conditions include obesity, diabetes, malignant hyperthermia, and fever. The construction of cell lines that express UCP-4 is also described.

BACKGROUND

Uncoupling protein (UCP-1; thermogenin) is a transmembrane proton-translocating protein present in the mitochondria of brown adipose tissue, a specialized tissue which functions in heat generation and energy balance (Nicolls, D. G., and Locke, R. M., *Physiol. Rev.* 64:2–40, (1984); Rothwell,. N. J. and Stock, M. J. *Nature*, 281:31–35 (1979)). Mitochondrial oxidation of substrates is accompanied by proton transport out of the mitochondrial matrix, creating a transmembrane proton gradient. Re-entry of protons into the matrix via ATP synthase is coupled to ATP synthesis. However, UCP-1 functions as a transmembrane proton transporter, permitting re-entry of protons into the mitochondrial matrix unaccompanied by ATP synthesis. Environmental exposure to cold evokes neural and hormonal stimulation of brown adipose tissue, which increases UCP-mediated proton transport, brown fat metabolic activity, and heat production.

Recent studies with transgenic models indicate that brown fat and UCP-1 have an important role in energy expenditure in rodents. Transgenic mice in which brown adipocyte tissue was ablated by a toxin coupled to the UCP-promoter developed obesity and diabetes (Lowell, B. B., et al., *Nature*, 366:740 (1993)). Obesity in these transgenic animals developed in the absence of hyperphagia, suggesting that the uncoupled mitochondrial respiration of brown fat is an important component of energy expenditure. In a separate transgenic mouse model, ectopic expression of UCP-1 in white adipose tissue of genetically-obese mice led to a significant reduction in body weight and fat stores (Kopecky J., et al., *J. Clin. Invest.* 96:2914–23, (1995)). These studies indicate that activity of UCP-1 is accompanied by energy expenditure and weight loss in rodents.

Two other UCP proteins have recently been cloned. The first uncoupling protein-like protein (UCPL) or UCP-2, is expressed in multiple tissues, and is enriched in tissues of the lymphoid lineage (Fleury, C., et al. *Nature Genetics*, 15:269–272, (1997)). The second, UCP-3, is predominantly localized to skeletal muscle (U.S. Ser. No. 60/043,407, filed Apr. 4, 1997, U.S. Ser. No. 60/046,154, filed May 8, 1997, and PCT/US98/005892 filed Mar. 25, 1998, all of which are hereby incorporated by reference herein; Boss, O., et al., (*FEBS Lett.* 408:3942, 1997). UCP-3 has been found to be regulated by cold and thyroid hormone (Larkin, S., et al., *Biochem. Biophys. Res. Comm.* 240:222–227, (1997)).

Thermogenic protein activity, such as that found with UCP-1, may be useful in reducing, or preventing the development of excess adipose tissue, such as that found in obesity. Obesity is becoming increasingly prevalent in developed societies. For example, approximately 30% of adults in the U.S. were estimated to be 20 percent above desirable body weight—an accepted measure of obesity sufficient to impact a health risk. (*Harrison's Principles of Internal Medicine* 12th Edition, McGraw Hill, Inc. (1991) p. 411). The pathogenesis of obesity is believed to be multifactorial, but the basic problem is that in obese subjects food intake and energy expenditure do not come into balance until there is excess adipose tissue. Attempts to reduce food intake, or to decrease hypernutrition, are usually fruitless in the medium term because the weight loss induced by dieting results in both increased appetite and decreased energy expenditure. (Leibel et al., *New England Journal of Medicine* 322:621–28, (1995)). The intensity of physical exercise required to expend enough energy to materially lose adipose mass is too great for many obese people to undertake on a sufficiently frequent basis. Thus, obesity is currently a poorly treatable, chronic, essentially intractable metabolic disorder. In addition obesity carries a serious risk of co-morbities including, Type 2 diabetes, increased cardiac risk, hypertension, atherosclerosis, degenerative arthritis, and increased incidence of complications of surgery involving general anesthesia. An increased level in thermogenesis in obese individuals, or individuals with a predisposition toward obesity should help to reduce the level of adipose tissue, and therefore avoid the complications associated with obesity.

Too high of a level of thermogenesis may also be detrimental for certain individuals, thus a method of decreasing the level of thermogenesis in such individuals is desirable. It would be desirable, for example, to treat or prevent conditions such as malignant hyperthermia, which occurs in approximately 1 in 50,000 anesthetic procedures, and can have about a 70% mortality rate. Studies in pigs, which are susceptible to malignant hyperthermia, have suggested that it may be caused by inappropriate activation of a sarcoplasmic reticulum Ca+ release channel (the ryanodine receptor) which then acts in a positive feedback manner to further release intracellular calcium and, thus affecting myotonic contraction and thermal overload (Mickelson, J. R., and Louis, C. F., *Physiol. Rev.* 76:537–92 (1996)). However, defects in the ryanodine receptor are found in only approximately 50% of patients with malignant hyperthermia (MacLennan, D. H., *Curr. Opin. Neurol.* 8:397–401 (1995)). There is discord between actual incidence and predicted genetic susceptibility based upon detection of mutant ryanodine receptors in some, but not all humans with malignant hyperthermia (MacLennan, D. H., *Curr. Opin. Neurol.*, 8:397–401 (1995)). Four chromosomal loci linked to malignant hyperthermia have been identified in familiar studies, but for only one has the genetic defect been localized to mutations of a particular gene, the ryanodine calcium channel gene on chromosome 19 (Id.; Steinfath, M., et al., *Anasthesiol. Intensivmed Notfallmed Schmerzther* 31:334–43 (1996)). It would therefore be useful to identify the protein involved in human malignant hyperthermia, and to design methods of regulating its expression to prevent or treat malignant hyperthermia.

Another condition where thermogenesis is increased is in fever, an increase in body temperature in response to infection or inflammation. Fever is observed not only in mammals and birds (warm-blooded animals; homeotherms), but also in some poikiothermic (cold-blooded) animals such as lizards, which increase their temperature behaviorally, by seeking warmer surroundings. Inoculated poikilothermic animals that are denied access to a warmer environment have a higher mortality, supporting a general advantage of being able to increase body temperature during infection. The mechanism underlying this advantage has been elusive, but may involve changes in properties of iron-binding proteins, resulting in a drop of free iron in body fluids, to which bacteria are particularly susceptible.

However, there are clinical settings in which fever is dangerous or unpleasant. These include epileptic patients where fever may precipitate convulsions; elderly patients with cardiac or cerebrovascular disease; children, who are at risk for febrile convulsions (which may then predispose to later epilepsy); patients with hyponutrition and chronic fever, where the increased metabolic demand of maintaining a higher body temperature compromises body energy stores; patients with fluid balance disturbances where the sweating associated with rapid up and down resetting of body temperature can exacerbate salt loss and electrolyte disturbance.

As opposed to the unregulated heat gain in malignant hyperthermia, exercise and heat-stroke, heat.gain in fever is a regulated event that recruits all of those mechanisms that are employed in normal autonomic and behavioral thermoregulation. From a control system perspective, there is a shift in body temperature set-point so that a higher body temperature is defended. Effector systems used to defend the higher body temperature in fever (shivering, non-shivering UCP-mediated thermogenesis, vasoconstriction, piloerection, warmth-seeking behaviors, heat-loss-lessening behaviors) are the same responses that are observed during cold exposure in non-febrile circumstances. Compounds that defeat one or more of these effector responses will be useful to reduce fever.

The present invention concerns a novel isolated uncoupling protein and nucleic acids coding for this protein, having some properties that differ from the properties of previously-identified uncoupling proteins.

SUMMARY OF THE INVENTION

The present invention concerns a novel uncoupling protein, which we have designated UCP-4, that is expressed in brain, heart, pancreas, and muscle tissue, as well as kidney, placenta, liver, lung, ovary, and spinal cord tissue, isolated nucleic acid molecules that encode UCP-4, as well as methods of screening for compounds that regulate the expression and/or the activity of UCP-4. Compounds that regulate the activity of UCP-4 will regulate thermogenesis, respiratory ATP synthesis, and energy utilization in brain, heart, pancreas, and muscle tissue, as well as kidney, placenta, liver, lung, ovary, and spinal cord tissue, and will be useful in treating or preventing diseases or conditions in which regulation of thermogenesis will be beneficial. Such conditions include, but are not limited to, obesity, diabetes, malignant hyperthermia, and fever. Our discovery that UCP-4 is present in brain and pancreas is consistent with a role in fuel sensing. UCP-2 is also found in parts of the brain, such as hypothalamic nuclei and the area postrema, that have a fuel-sensing function. A fuel-sensing function is likely to require tissue to have a high metabolic rate so that its ionic milieu becomes susceptible to fuel availability. The output of fuel sensors in the brain and in other tissues, such as the pancreas, will ultimately drive responses that will tend to correct disturbances in body energy content. Compounds that act upon UCP-4 to mimic the sensing of hypernutrition (body energy excess) will trigger energy minimizing responses (e.g., thermogenesis, decreased energy intake) and will be useful in the treatment of metabolic diseases characterized by hypernutrition, such as diabetes and obesity. Compounds that act upon UCP-4 to mimic undernutrition will trigger energy-maximizing responses (such as food ingestion and conservation of body energy stores) and will be useful in treating conditions characterized by a depletion of body energy stores (e.g., anorexia nervosa, malnutrition and cachexia).

Thus, one embodiment of the invention comprises isolated nucleic acid molecules which encode UCP-4. The encoded UCP-4 may be the UCP-4 sequence encoded in any eukaryotic cell, preferably a vertebrate cell, more preferably a mammalian cell. In one preferred aspect, the invention provides an isolated nucleic acid molecule which encodes rat UCP-4. In another preferred aspect is an isolated nucleic acid molecule which encodes mouse UCP-4. Especially preferred are nucleic acid molecules which encode human UCP-4. In more preferred aspects, said nucleic acid encodes an amino acid sequence comprising the amino acid sequence of FIG. 1. In most preferred aspects, said nucleic acid molecule comprises the nucleic acid sequence of FIG. 1. The term "UCP-4" includes, but is not limited to, all isoforms thereof, generated by alternative splicing of the primary transcript that gives rise to a nucleotide sequence that encodes the amino acid sequence shown in FIG. 1.

In another embodiment of the present invention, a nucleic acid molecule encoding UCP-4 is operably linked to a promoter sequence, wherein said promoter sequence promotes the transcription of the coding region of said nucleic acid.

Also provided in the present invention, are vectors comprising a nucleic acid molecule of the present invention. In preferred aspects, said vectors further comprise a promoter sequence which is operably linked to said nucleic said molecule. In more preferred embodiments, said vectors further comprise a 3' polyadenylation sequence which is operably linked to said nucleic acid molecule. Also within the scope of the present invention are host cells transformed with the nucleic acid molecules or vectors of the present invention. The UCP-4-expressing host cell is preferably a yeast cell, CHO cell, COS cell, NIH3T3 cell, HEK-293 cell, or 3T3L1 cell.

In another embodiment of the invention, isolated UCP-4, is provided. The UCP-4 may be, for example, isolated from a cell that comprises an endogenous nucleic acid molecule that encodes UCP-4. The UCP-4 may be isolated from a cell that expresses UCP-4 from a heterologous nucleic acid molecule, such as in a transformed cell. The cell may be eukaryotic or prokaryotic. Preferably the cell is a bacterial, insect, yeast, CHO, COS, NIH3T3, HEK-293, or 3T3L1 cell. Alternatively, UCP-4 may be synthesized by methods known to those skilled in the art, including, but not limited to UCP-4 that is expressed in, and/or isolated from a cell-free translation system, or isolated through chemical synthesis.

In another embodiment of the present invention anti-UCP-4 antibodies are provided. Preferably these antibodies bind to an amino acid sequence that is not completely homologous among all three UCPs. More preferably these antibodies bind to a region comprising amino acids 38–51 of said UCP-4 sequenceor to a region comprising amino acids 93–107 of said UCP-4 sequence. More preferably, the anti-UCP-4 antibody is a monoclonal antibody;

In yet other embodiments of the present invention are provided methods of gene therapy comprising administering to a subject a nucleic acid molecule that encodes UCP-4. In one preferred aspect is provided a method of increasing thermogenesis in a subject, comprising administering to said subject a nucleic acid molecule which encodes UCP-4, wherein said administering of said nucleic acid molecule increases the level of UCP-4 expression in one or more tissues of said subject. Preferably, said tissue is brain, heart, pancreas, muscle, kidney, placenta, liver, lung, ovary, or spinal cord tissue. More preferably said tissue is brain, heart, pancreas, or muscle tissue. Said method is preferably for purposes of treating obesity, diabetes, and/or decreasing fat in a subject. Other methods of gene therapy provided in the present invention are methods for decreasing expression of UCP-4 in a subject by administering to said subject an antisense nucleic acid molecule wherein said administering of said nucleic acid molecule decreases the level of UCP-4 expression in one or more tissues of said subject. Preferably said method is used for decreasing malignant hyperthermia, or fever, in said subject. Preferably said tissue is brain, heart, pancreas, muscle, kidney, placenta, liver, lung, ovary, or spinal cord tissue. More preferably, said tissue is brain, heart, pancreas, or muscle tissue.

Another embodiment of the invention comprises a method of screening for a compound that binds to or modulates the activity of UCP-4, comprising
  a) introducing said UCP-4 and one or more test compounds into an acceptable medium, and
  b) monitoring the binding or modulation by physically detectable means,
  c) thereby identifying those compounds that bind to or modulate the activity of said UCP-4.

In one preferred aspect, UCP-4 is associated with a mitochondrial membrane. In another preferred aspect, said monitoring of the binding or modulation of said compound to UCP-4 further comprises monitoring the level of purine nucleotide binding of UCP-4 in the presence of said compound or compounds; and identifying the compounds that, when in the presence of UCP-4, alter the level of purine nucleotide binding to UCP-4. Preferably, said purine nucleotide is GDP. In other preferred aspects, the method further comprises monitoring the level of purine nucleotide binding of UCP-4 in the absence of said compound or compounds.

In another preferred aspect of the invention, said monitoring of the binding to or modulation of UCP-4 by said compound further comprises monitoring the level of fatty acid binding of UCP-4 in the presence of said compound; and identifying the compounds that, when in the presence of UCP-4, alter the level of fatty acid binding to UCP-4. Preferably, said fatty acid is laurate. In other preferred aspects, said monitoring further comprises monitoring the level of fatty acid binding of UCP-4 in the absence of said compound.

In another preferred embodiment of the invention, a method is provided for screening for a compound that binds to or modulates the activity of UCP-4, comprising monitoring the effect of said compound on a cell that expresses UCP-4.

In one preferred aspect, the cell that expresses UCP-4 is present in brain, heart, pancreas, muscle, kidney, placenta, liver, lung, ovary, or spinal cord tissue. Preferably, the cell that expresses UCP-4 is present in brain, heart, pancreas, or muscle tissue. Preferably, the cell that expresses UCP-4 is transformed with a nucleic acid encoding UCP-4. The nucleic acid may preferably be operably limited to the UCP-4 native promoter, or to a heterologous promoter. By "heterologous promoter" is meant any promoter that allows the expression of UCP-4, that is not the endogenous UCP-4 promoter. More preferably, the nucleic acid encodes an amino acid sequence comprising the amino acid sequence of FIG. 1.

In another preferred embodiment, the nucleic acid comprises the nucleic acid sequence of FIG. 1. In another preferred embodiment, the method further comprises monitoring the effect of said compound on a cell that does not express UCP-4. Preferably, said cell that does not express UCP-4 is otherwise substantially genetically identical to said cell that-expresses UCP-4.

One preferred method of monitoring of the effect of said compound on said cell comprises monitoring the level of mitochondrial respiration of said cell. Other preferred methods comprise monitoring the level of mitochondrial respiration in isolated mitochondria. Most preferred methods comprise monitoring the level of mitochondrial respiration or whole animals, preferably mammals, more preferably rats or mice, and most preferably humans. In another preferred method, the monitoring of the effect of said compound on said cell comprises monitoring the level of mitochondrial membrane purine nucleotide binding, preferably GDP, of said cell.

In another preferred method, said monitoring of the effect of said compound on said cell comprising monitoring the level of fatty acid, preferably laurate.

In preferred embodiments, said UCP-4 of the present invention, and used in the methods of the present invention, as well as UCP-4 encoded by the nucleic acids used in the methods of present invention, is human UCP-4. Preferably, said UCP-4 comprises the amino acid sequence of FIG. 1. Most preferably, said UCP-4 is encoded by a nucleic acid molecule comprising the nucleic acid sequence of FIG. 1. The term "UCP-4" also includes the various isoforms of UCP-4 due to variations in the splicing of the RNA transcript coding for UCP-4. UCP-4s that contain post-translational modifications that are required for activity or modulate activity are also within the scope of the present invention.

The compound that regulates UCP-4 activity may be found to either increase or decrease UCP-4 activity.

In another preferred embodiment, a method is provided for screening for a compound that regulates the expression of UCP-4, comprising monitoring the effect of said compound on the level of expression of UCP-4 RNA in a cell that expresses UCP-4. Preferably, the cell that expresses UCP-4 is present in brain, heart, pancreas, muscle, kidney, placenta, liver, lung, ovary, or spinal cord tissue. More preferably the cell is present in brain, heart, pancreas, or muscle tissue. Preferably, the cell that expresses UCP-4 is transformed with a nucleic acid encoding UCP-4. More preferably, said nucleic acid encodes an amino acid sequence comprising the amino acid sequence of FIG. 1. Most preferably, the nucleic acid comprises the nucleic acid sequence of FIG. 1. In one preferred aspect, the nucleic acid molecule is operably linked to a UCP-4 promoter. In another preferred aspect, the nucleic acid molecule is operably linked to a heterologous promoter. In another preferred aspect, the method utilizes a yeast cell that is transformed with a nucleic acid that encodes UCP-4. In more preferred aspects, said cell is a transformed eukaryotic cell, preferably a vertebrate cell, more preferably a mammalian cell, such as those known to those of skill in the art, and those described herein. In other preferred aspects, said cell is a transformed yeast cell. Preferably, the methods involve determining whether the expression of said messenger RNA is increased or decreased compared to the expression of said messenger RNA in a cell that has not been exposed to said compound. Preferably, said UCP-4 is human UCP-4. More preferably, said UCP-4 is encoded by a nucleic acid sequence comprising the nucleic acid sequence of FIG. 1.

In one preferred aspect, the level of UCP-4 RNA is determined by probing the messenger RNA expressed in said cell with a nucleotide probe that comprises a nucleotide sequence that is homologous to at least 15, preferably 30, more preferably 45, consecutive nucleotides of a UCP-4 nucleotide sequence. Preferably, said nucleotide probe does not substantially bind under high stringency conditions to any non-UCP-4 nucleotide sequence in the same tissue. By "high stringency hybridization conditions" is meant those hybridizing conditions that (1) employ low ionic strength and high temperature for washing, for example, 0.0 15 M NaCl/0.0015 M sodium citrate/0.1% SDS at 50 C; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42 C; or (3) employ 50% formamide, 5×SSC (0.75 M NaCl, 0.075 M sodium citrate, pH 7.0, 5×Denhardt's solution, sonicated salmon sperm DNA (50 μg/ml), 0.1% SDS, and 10% dextran sulfate at 42 C, with washes at 42 C in 0.2×SSC and 0.1% SDS. Under stringent hybridization conditions only highly complementary nucleic acid sequences hybridize. Preferably, such conditions prevent hybridization of nucleic acids having 1 or 2 mismatches out of 20 contiguous nucleotides binding of said cell.

In other methods of the present invention, the effect of a compound on the level of expression of UCP-4 is further monitored on a cell that does not express UCP-4 thus, providing a negative control. Preferably, said cell that does not express UCP-4 is otherwise substantially genetically identical to said cell that expresses UCP-4.

The compound may either increase or decrease the expression of UCP-4. In other aspects, the compound may bind to a transcriptional regulatory sequence that increases or decreases the expression of UCP-4 RNA.

In another embodiment of the invention, a method is provided for screening for a compound that regulates the expression of UCP-4 in a fuel-sensing tissue. Such fuel-sensing tissues include, but are not limited to brain tissue, such as, for example, hypothalamic nuclei and the area postrema. Compounds may increase or decrease UCP-4 activity in a fuel-sensing tissue. Thus, a method is provided for treating a condition or disorder that can be ameliorated by increasing energy-minimizing responses (such as heat-wasting or inhibition of food intake) in a subject comprising administering to the subject a therapeutically effective amount of a compound that increases UCP-4 activity in a fuel-sensing tissue.

A method is also provided for treating a condition or disorder that can be ameliorated by increasing energy-maximizing responses (such as promoting food ingestion or conserving body energy stores) in a subject comprising administering to the subject a therapeutically effective amount of a compound that decreases UCP-4 activity in a fuel-sensing tissue.

In another embodiment of the invention is provided a method for treating conditions or disorders that can be ameliorated by increasing the level of thermogenesis in a subject, for example obesity, comprising administering to said subject a therapeutically effective amount of a compound that increases the activity of UCP-4. In one aspect, said condition or disorder is obesity. In another aspect, said condition or disorder is diabetes. By condition or disorder is meant a disease, condition, or disorder, or a susceptibility to the same.

In another embodiment of the invention is provided a method for treating conditions or disorders that can be ameliorated by decreasing the level of thermogenesis in a subject, for example, in a subject with a susceptibility to malignant hyperthermia, or fever, comprising administering to said subject a therapeutically effective amount of a compound that decreases the activity of UCP-4.

Also provided within the scope of the present invention is a method of preventing or treating diseases or conditions related to a decrease in thermogenesis, such as obesity, in a subject comprising administering to said subject a therapeutically effective amount of a compound that increases UCP-4 activity in said subject. Preferably, increase in said UCP-4 activity occurs in a tissue, preferably the brain, heart, pancreas, muscle, kidney, placenta, liver, lung, ovary or spinal cord tissue, more preferably the brain, heart, pancreas, or muscle tissue of said subject. Said increase in UCP-4 activity may be associated with, for example, an increase in UCP-4 activation. Said compound may the alter post-translational modification of UCP-4. Alternatively, said increase in UCP-4 activity is associated with an increase in UCP-4 gene expression.

Also provided within the scope of the present invention is a method of regulating insulin secretion by administering a compound that increases or decreases the activity of UCP-4. Preferably, said UCP-4 activity occurs in the pancreas or the area postrema. Such increase or decrease in UCP-4 activity may be associated with, for example, an increase or decrease in UCP-4 activation or in UCP-4 gene expression.

A method is also provided of preventing or treating diseases or conditions related to thermogenesis such as malignant hyperthermia or fever in a subject comprising administering to said subject a therapeutically effective amount of a compound that decreases the activity of UCP-4. Said compound may alter the post-translational modification of UCP-4. Alternatively, said decrease in UCP-4 activity is associated with a decrease in UCP-4 gene expression.

Diagnostic methods are also provided in the present invention. In one embodiment, a method is provided for determining whether a subject has a susceptibility to a condition or disorder related to thermogenesis, such as, for example, malignant hyperthermia or obesity, comprising: probing the messenger RNA expressed in a tissue of said subject with a nucleotide probe that comprises a nucleotide sequence that is homologous to at least 15, preferably at least 30, more preferably at least 45, consecutive nucleotides of a UCP-4 nucleotide sequence; and determining whether said messenger RNA expression is increased compared to the messenger RNA in a subject that does not have a susceptibility to malignant hyperthermia. Preferably the nucleotide probe does not bind to any non-UCP-4 nucleotide sequence in the same tissue. Preferably, the nucleotide sequence is homologous to at least 10 consecutive nucleotides of a human UCP-4 sequence. In other diagnostic methods of the present invention, techniques known to those skilled in the art, such as PCR and sequencing, may be used to locate one or more point mutations or deletions in the UCP-4 gene in subjects to determine whether the subject has a susceptibility to a condition or disorder related to thermogenesis. Said mutation or deletion may or may not affect the expression level of UCP-4 RNA, but may affect the activity of UCP-4. Thus, in one aspect of the invention, a method is provided for determining whether a subject has a condition or disorder related to UCP-4 structure comprising: a) probing the RNA in a tissue of said subject with a nucleotide probe that comprises a nucleotide sequence that is homologous to at least 15 consecutive nucleotides of a UCP-4 nucleotide sequence; b) isolating the RNA bound to said probe; c) obtaining the sequence of said RNA; and d) comparing said sequence to the UCP-4 RNA of a subject without said condition or disorder or a subject with said condition or disorder.

A method is also provided for determining whether a subject has a condition or disorder related to a defect in the expression level of UCP-4 in a tissue of said subject comprising determining the level of UCP-4 present in said tissue and comparing said level of UCP-4 with the level of UCP-4 in a subject that does not have a condition or disorder related to a defect in the expression level of UCP-4. In a preferred aspect, said level of UCP-4 present in said tissue is determined by probing said tissue with an antibody, preferably a monoclonal antibody, that recognizes UCP-4.

In preferred aspects, the subject is determined to have a condition or disorder related to obesity or diabetes if said defect in the expression level of UCP-4 in said tissue of said subject results in a decreased level of UCP-4 as compared to a subject that does not have a condition or disorder related to obesity or diabetes said subject is determined to have a susceptibility to hyperthermia if said defect in the expression level of UCP-4 in said tissue of said subject results in an increased level of UCP-4 as compared to a subject that does not have a susceptibility to hyperthermia. In other preferred aspects, said subject may be determined to have a condition or disorder related to thermogenesis if said subject is found to have one or more deletions or point mutations in the UCP-4 gene. Said deletion or mutation may or may not affect the expression level of UCP-4 RNA, but may affect the activity of UCP-4.

BRIEF DESCRIPTION OF THE DRAWINGS

Figure Legends

FIG. 1: Nucleotide sequence, (SEQ ID NO. 1) and deduced amino acid sequence (SEQ ID NO. 2) of human UCP-4. The nucleotide numbering scheme is presented along the right margin. The sixth transmembrane domain (Klingenberg, M., *Trends Biochem Sci.* 15:108–112,1990) is underlined. The putative purine nucleotide recognition element is boxed (Murdza-Inglis, D. L., et at., *J. Biol Chem.* 269:7435–7438, 1994; Bouillaud, F., et al., *EMBO J.* 13:1990–1997, 1994). The deduced amino acid sequence is shown below the nucleotide sequence. The standard one letter abbreviations for amino acids are used: A, alanine; C, cysteine; D, aspartic acid; E, glutamic acid; F, phenylalanine; G, glycine; H, histidine; I, isoleucine; K, lysine; L, leucine; M, methionine; N, asparagine; P, proline; Q, glutamine; R, arginine; S, serine; T, threonine; V, valine; W, tryptophan; Y, tyrosine.

FIG. 2: Alignment of human UCP-1, human UCP-2 and human UCP-3 with human UCP-4. Amino acid identities with human UCP-4 are shaded. The numbering scheme of the amino acids for the four proteins is shown in the left margin.

FIGS. 4A and 4B: A) Tissue distribution of human UCP-4 transcripts. Total RNA dot blot analysis of human UCP-4 gene transcripts. The blot was probed with a human UCP-4 DNA fragment, washed in 0.2×SSC/0.1% SDS at 50 C and exposed to film for 6 days. B) key to the human RNA dot blot showing the tissue at each position.

DETAILED DESCRIPTION OF THE INVENTION

Figure 3:
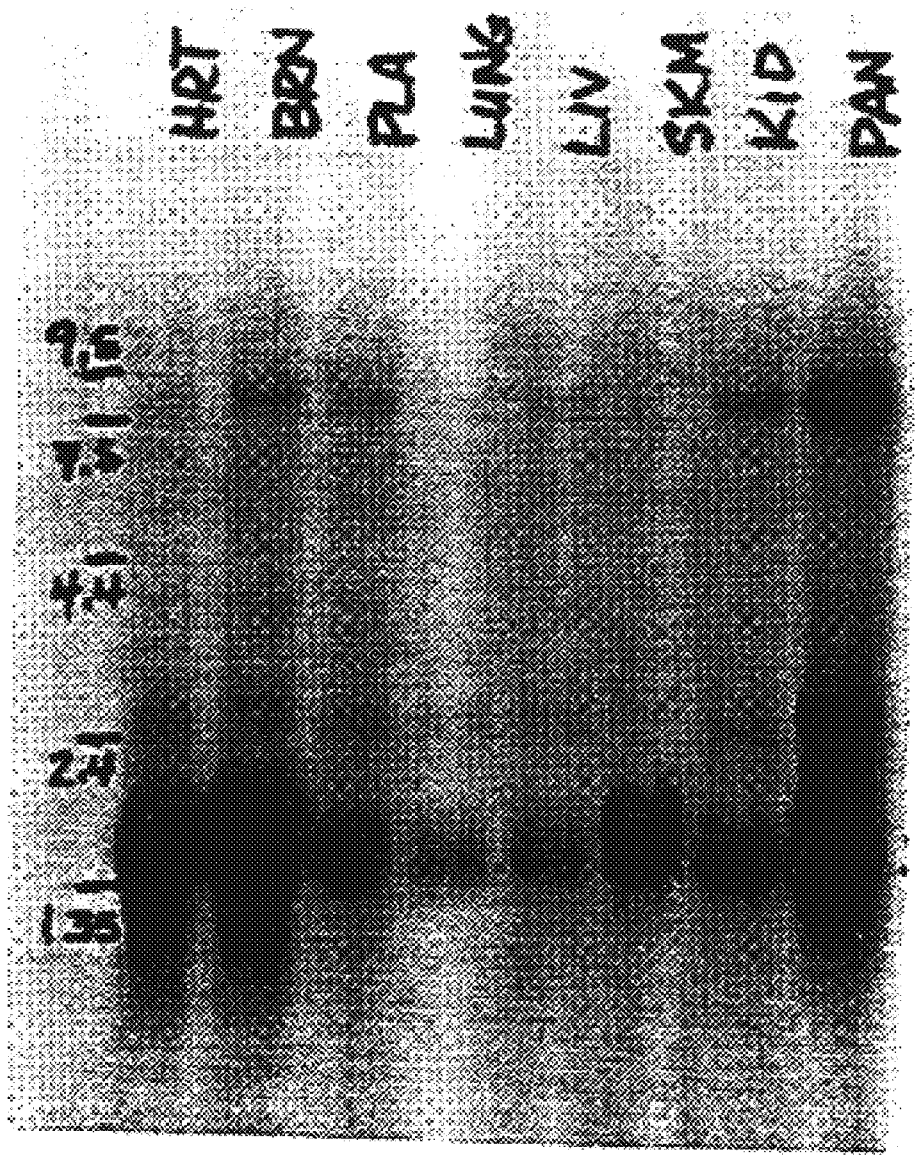
FIG. 3: Tissue distribution of human UCP-4 transcripts. Northern blot analysis of poly (A)+ RNA from human tissues hybridized with a UCP-4-specific probe and washed at high stringency (0.2×SSC, 0.1%SDS, 50 C). Abbreviations: HRT, heart; BRN, brain; PLA, placenta; LUN, lung; LIV, liver; SKM, skeletal muscle; KID, kidney; PAN, pancreas. RNA size markers: 9.49, 7.46, 4.40, 2.37 and 1.35 kilobases.

It has now been demonstrated that a novel uncoupling protein is present in brain, heart, pancreas, and muscle tissue, as well as kidney, placenta, liver, lung, ovary, and spinal cord tissue. This uncoupling protein, UCP-4, may be used to screen for compounds that regulate the activity of UCP-4. Such compounds are likely to regulate thermogenesis.

The identification, characterization, and cloning of UCP-4 is presented in Example 1. The sequence homology to the sequence of other uncoupling proteins described in this example suggests that UCP-4 may have a similar function to UCP-1 and other uncoupling proteins (e.g., UCP-2 and UCP-3) in mediating mitochondrial proton transport.

Compounds that enhance the activity of UCP-4 will stimulate thermogenesis and energy utilization, and will be useful in treating obesity and diabetes. The sequence of human UCP-4, reported here, may be used in the construction of cell lines expressing this protein. These cell lines will be useful in screening for compounds which regulate the activity or expression of UCP-4, including, but not limited to, human UCP-4.

Example 2, which explores the tissue specificity of human UCP-4 expression, indicates that UCP-4 is expressed predominantly in brain, heart, pancreas, and muscle tissue. Northern blot analysis of human tissues indicates that UCP-4 is detected in brain, heart, pancreas, and skeletal muscle, and to a lesser extent in kidney, placenta, liver, and lung. Total RNA dot blot analysis reveals that UCP-4 is also detected in ovary, spinal cord, and other tissues, but is absent from spleen and lymph node. These results demonstrate that the tissue-specific distribution of human UCP-4 transcripts is unique and not shared by the other members of this uncoupling protein family. Human UCP-1 has long been established to be expressed solely in brown adipose tissue, whereas human UCP-3 transcripts are predominantly localized to skeletal muscle (Boss, O., et al. 1997. Uncoupling protein-3: a new member of the mitochondrial carrier family with tissue-specific expression (*FEBS Lett.* 408:39–42; Larkin, S., et al. 1997. Regulation of the third member of the uncoupling protein family, UCP3, by cold and thyroid hormone. *Biochem. Biophys. Res. Comm.* 240:222–227). UCP-2 transcripts are expressed in multiple tissues and enriched in tissues of the lymphoid lineage, but are observed at only low levels in brain (Fleury, C., et al. 1997. Uncoupling protein-2: a novel gene linked to obesity and hyperinsulinemia. *Nature Genetics* 15:269–272).

Expression of UCP-4 at relatively high levels in the pancreas indicates involvement in regulation of energy metabolism in the pancreas. Alteration of UCP-4 activity in pancreatic islets will allow regulation of insulin secretion.

Expression of UCP-4 in the brain may indicate involvement in regulation of energy metabolism in the brain, for example, in the area postrema region of the brain. Alteration of UCP-4 action in the brain may allow regulation of insulin secretion.

Example 3 demonstrates a method for determining whether UCP-4 is activated by environmental conditions, such as cold temperatures and by $T_3$, indicating an involvement in muscle energy utilization and thermogenesis. Example 4 demonstrates the use of UCP-4 to screen for compounds that regulate UCP-4 activity.

As in Example 1, and elsewhere herein, the nucleotide sequence for UCP-4 (FIG. 1) will be useful in constructing cell lines expressing UCP-4, for example, by transfection with a suitable expression vector encoding UCP-4. The sequence will also be useful for identifying cells containing UCP-4. Cells expressing UCP-4, either by transfection or endogenously, may be useful in screening for compounds which increase mitochondrial respiration mediated by UCP-4. Expression of UCP-4 in a mammalian cell line where UCP-4 is not normally found, such as CHO (Chinese hamster ovary), COS, NIH3T3, HEK-293 or 3T3L1 cell lines could be achieved using standard methods of stable transfection (Sambrook et al., *Molecular Cloning, A Laboratory Manual*, Second Edition, Volumes 1 to 3, Cold Spring Harbor Laboratory Press, 1989). A vector would be constructed containing UCP-4 that allows inducible expression of UCP-4 in response to for instance the glucocorticoid analog dexamethasone or in response to removal of the antibiotic tetracycline. These inducible promoter systems are available commercially (Pharmacia and Clontech). Expression of UCP-4 in an inducible system allows the cells to grow normally in the absence of the predicted warming effects of ectopic expression of UCP-4 until the cells are at sufficient density to be used for the screening application, at which time UCP-4 expression may be readily induced. Alternatively, UCP-1 and now UCP-2 have successfully been expressed in yeast (Murdza-Inglis, D. L., Patel, H. V., Freeman, K. B., Jezek, P., Orosz, D. E. and Garlid, K. D. 1991. Functional reconstitution of rat uncoupling protein following its high level expression in yeast (*JBC*, 260:1 1871–11875; Bathgate, B., Freebaim, E. M., Greenland, A. J, and Reid, G. A. 1992.) Functional expression of the rat brown adipose tissue uncoupling protein in *Saccharomcyces cerevisiae* (*Mol. Microbiol.* 6:363–370; Fleury, C., Neverova, M., Collins, S., Raimbault, S., Champigny, O., Levi-Meyrueis, C., Bouillaud, F., Seldin, M. F., Surwit, R. S., Ricquier, D. and Warden, C. H. 1997). Uncoupling protein-2: a novel gene linked to obesity and hyperinsulinemia (*Nature Genetics*, 15:269–272). Yeast vectors for the expression of UCP-4 in yeast would consist of an inducible promoter system such as the galactokinase gene enhancer/promoter, GAL1 (Mumberg, D., Muller, R. and Funk, M. 1994. Regulatable promoters of *Saccharomyces cerevisiae*: comparison of transcriptional activity and their use for heterologous expression (*Nucleic Acids Res.* 22:5767–5768). In this system transcription is tightly repressed by addition to the growth medium of glucose but upon addition of galactose expression is induced to high levels. Deletions of this promoter and/or use of different plasmid types that direct replication to high or low copy numbers will allow expression levels of UCP-4 to be varied to achieve those optimal for both yeast survival and UCP-4 detection (Mumberg, D., Muller, R. and Funk, M. 1994. Regulatable promoters of *Saccharomyces cerevisiae*: comparison of transcriptional activity and their use for heterologous expression (*Nucleic Acids Res.* 22.5767–5768). The UCP-4 cDNA can also be modified so as to be optimal for expression in yeast cells: work with UCP-1 has shown that removal of the 5' and 3' untranslated regions of UCP-1 cDNA and modification of the UCP-1 sequence surrounding the methionine start codon to more closely resemble that normally found in yeast genes greatly improves expression levels in yeast (Murdza-Inglis, D. L., Patel. H. V., Freeman, K. B., Jezek, P., Orosz, D. E. and Garlid, K. D. 1991. Functional reconstitution of rat uncoupling protein following its high level expression in yeast. *JBC* 260:11871–11875); Bathgate, B., Freebaim, E. M., Greenland, A. J, and Reid, G. A. 1992 Functional expression of the rat brown adipose tissue uncoupling protein in *Saccharomcyces cerevisiae. Mol. Microbiol.* 6:363–370). These modifications can be readily achieved using PCR mutagenesis approaches such as are well known to those skilled in the art. In either case, yeast expression or mammalian expression, the UCP-4 gene can be additionally engineered, or not, by in frame addition, at the carboxy terminus of the UCP-4 cDNA, of an oligonucleotide sequence encoding a short peptide that is a characterized epitope, such as the commercially available FLAG system (Eastman Kodak Comp., New Haven, Conn.). This allows UCP-4 protein expression level and mitochondrial targeting to be monitored by the use of commercially available antibodies directed against the peptide epitope. The qualitative properties of yeast lines containing epitope tagged vs. wildtype UCP-4 will be compared to confirm that the peptide tag does not interfere with normal function. The recombinant UCP-4 containing yeast cells or mammalian cell lines can be expanded under non-inducing conditions and prior to screening subjected to induction to allow UCP-4 protein production and insertion into mitochondrial membranes. Compounds (UCP-4 activators) may be identified by comparing their ability to stimulate respiration or metabolic activity of UCP-4-expressing cells, compared to control cells, which may be untransfected cells of the same genetic background. Alternatively, isolated mitochondrial preparations could be used to screen for UCP-4 activators, either by measuring stimulation of respiration, or by measuring mitochondrial swelling in a suitable buffer system.

A baculovirus expression system may also be used to express and isolate the UCP-4 proteins of the present invention. The baculovirus system uses virus-infected insect cells, such as Sf9 cells, to express a protein of interest. Such methods are known to those of ordinary skill in the art and may be found in, for example, O'Reilly et al., *Baculovirus Expression Vectors: A Laboratory Manual*, W.H. Freeman, New York,.(1992).

Included in the methods of the present invention are methods of identifying compounds that bind to UCP-4. Compounds that bind to UCP-4 are likely to be involved in regulating UCP-4 activity. Protein or peptide binding assays are known to those skilled in the art, and include, but are not limited to, those that measure co-precipitation, co-migration on non-denaturing SDS-PAGE, and co-migration on Western blots. Binding assays are described in, for example, Bennet, J. P. and Yamamura, H. I., Neurotransmitter, hormone, or drug receptor binding methods in *Neurotransmitter Receptor Binding* pp. 61–89 (Yamamura, H. I., et al., eds. 1985). Studies with UCP-1 suggest an additional method for identifying activators. UCP-mediated transport is inhibited by certain purine nucleotides, notably diphosate and triphosphate purine nucleotides, especially GDP, which bind to and occupy an inhibitory site on the protein (Murdza-Inglis, D. L., et al., *J. Biol. Chem.* 269:7435–38 (1994); Bouillaud, F., et al., *EMBO J.* 13:1990–97 (1994)). Compounds may occupy this site and prevent nucleotide-mediated inhibition of UCP-1function, and these compounds may be identified by their ability to inhibit radiolabeled purine nucleotide binding to UCP-containing membranes. Because the amino acid sequence homology of UCP-4 to UCP-1 is reasonably well conserved in the nucleotide inhibitory site, and especially in amino acid residues known to be critical for purine nucleotide binding, then UCP-4 activators may be identified by a similar method. By this method, compound libraries are screened for their ability to inhibit radiolabeled nucleotide binding to UCP-4-containing membranes. Lead compounds may be further tested and optimized for their ability to reduce nucleotide-mediated inhibition of UCP-4 function in vitro, and to stimulate thermogenesis and weight loss in vivo in suitable animal models.

In an additional method for identifying activators, the fatty acid binding of UCP-4 in the presence or absence of a test compound may be compared. UCP-1 proton transport activity is also regulated by fatty acids. Adrenergic stimulation predominantly via 3 adrenergic receptors on the cell surface results in increased cAMP levels in the cell and thus stimulation of cAMP-dependent protein kinase (PKA). Activated PKA causes increased lipoprotein lipase activity and thus release of free fatty acids. In vitro UCP-1 can function as a fatty acid anion transporter and it is believed that fatty acids stimulate proton transport across the membrane by themselves mediating the transport of protons as UCP-1-bound protonophores (Garlid, K. D., et al., *JBC*, 271:2615–2620 (1996)) The fatty acid binding domain has been localized to the carboxy terminus by site directed mutagenic studies (Gonzalez-Barroso, M. M., et al., *Eur. J. Biochem.*, 239:445–450 (1996)).

In another method for identifying activators of UCP-4, the effects of test compounds on the area postrema region of the brain are compared. Methods of screening for compounds useful in the treatment of metabolic disorders are described and claimed in PCT US/99/15861 filed Jul. 13, 199, titled "The Use of Membranes, Cells and Tissue From the Area Postrema to Identify Therapeutic Compounds" the contents of which are incorporated herein by this reference, and which application is commonly owned with the present application.

The screening methods described herein may employ naturally expressed, cloned, or synthesized UCP-4. UCP-4 derivatives or analogs may also be used in the screening methods described herein. High-throughput screening of chemical libraries using cells stably transfected with UCP-4 may offer a promising approach to identify new lead compounds which are active on UCP-4 (Knopfel et al., *J. Med. Chem.* 38:1417, (1995)). These lead compounds serve as templates for extensive chemical modification studies to further improve potency, and important therapeutic characteristics such as bioavailability.

It will be appreciated by those in the art that there are various methods useful in preparing and isolating nucleic acids that encode UCP-4. In general, chemical synthesis of DNA and recombinant DNA isolation techniques are now well known. An extensive discussion embodying a number of commonly used methodologies can be found in Sambrook et al., *Molecular Cloning, A Laboratory Manual, Second Edition*, Volumes 1 to 3, Cold Spring Harbor Laboratory Press 1989). Recombinant methods allow segments of genetic information, DNA, from different organisms, to be joined together outside of the organisms from which the DNA was obtained and this hybrid DNA to be incorporated into a cell that will allow the production of the protein for which the original DNA encodes. Genetic information encoding a protein of the present invention may be obtained from genomic DNA, mRNA (preferably brain, heart, pancreas, or skeletal muscle tissue mRNA), or total tissue RNA (preferably brain, heart, pancreas, or skeletal muscle tissue total RNA) of an organism by methods well known in the art. Preferred methods of obtaining this genetic information include isolating mRNA from an organism, converting it to its complementary DNA, incorporating the cDNA into an appropriate cloning vector, and identifying the clone which contains the cDNA encoding the desired protein by means of hybridization with appropriate oligonucleotide probes constructed from known or postulated sequences of the protein. Especially preferred methods of obtaining this genetic information include isolating total tissue RNA, preferably brain, heart, pancreas, or skeletal muscle tissue total RNA, from an organism, converting it to its complementary DNA, and amplifying, detecting and isolating a cDNA sequence encoding the desired protein. The genetic information in the cDNA encoding a protein of the present invention may be ligated into an expression vector, the vector introduced into host cells, and the genetic information expressed as the protein encoded for.

Thus, nucleic acids encoding the proteins of the invention may be cloned by incorporating a DNA fragment coding for UCP-4 in a recombinant DNA vehicle, typically, for example, mammalian, yeast, insect, bacterial or viral vectors, and transforming a suitable host, for example, an *E. coli*, an insect, or *S. cerevisae* cell line and isolating clones incorporating the recombinant vectors. Such clones may be grown and used to produce UCP-4.

Mixtures of mRNA can be isolated from eukaryotic cells and double-stranded DNA copies of entire genes synthesized which are complementary to the isolated mRNA. mRNA is first reverse-transcribed to form a single-stranded cDNA by an RNA-directed DNA polymerase, e.g., reverse transcriptase. Reverse transcriptase synthesizes DNA in the 5' to 3' direction, utilizes deoxyribonucleoside 5'-triphosphates as precursors, and requires both a template and a primer strand. By a series of additional reactions, double-stranded cDNA is produced and inserted into cloning or expression vectors by any one of many known techniques, which depend at least in part on the vector selected. Expression vectors refer to vectors which are capable of transcribing and translating DNA sequences contained therein, where such sequences are linked to other regulatory sequences capable of effecting their expression. These expression vectors are replicable in the host organisms or systems as either plasmids, bacteriophage, or as an integral part of the chromosomal DNA. Recombinant vectors and methodology are in general well known and suitable for use in host cells over a wide range of prokaryotic and eukaryotic organisms. The cDNA cloning and expression procedures further described below and in the Examples are but some of a wide variety of well established methods to produce specific sequences and reagents useful in the invention.

One method of preparing the products of the invention includes the steps of constructing a vertebrate cDNA library, preferably a vertebrate brain, heart, pancreas, or skeletal muscle cDNA library; ligating the cDNA library into a cloning vector; introducing the cloning vector containing the cDNA library into a first host cell; contacting the cDNA molecules of the first host cell with a solution containing a suitable UCP-4 gene hybridization probe; detecting and then isolating a cDNA molecule which hybridizes to the UCP-4 gene hybridization probe; ligating the hybridizing cDNA molecule into an expression vector; transforming a second host cell with the expression vector containing the cDNA molecule which encodes UCP-4; culturing the transformed second host cell under conditions that favor the production of UCP-4, and isolating the UCP-4 expressed by the second host cell.

The nucleic acid molecule products of the invention may also be prepared by the method described in Example 1. The isolated nucleic acid molecules encoding UCP-4 include, but are not limited to, DNA, mRNA, cDNA, and variants which use, for example, preferred codons for expression in various cells or tissues. Such preferred codons are disclosed in, for example, Grantham et al., *Nuc. Acids Res.*, 9:43–74 (1981), and Lathe, *J. Mol. Biol.*, 183:1–12 (1985). These articles, and all other publications referenced herein, are hereby incorporated in their entirety by reference. The modifications can be readily achieved using PCR mutagenesis approaches such as are well known to those skilled in the art.

Preferred natural sources of mRNA from which to construct a cDNA library are brain, heart, pancreas, and muscle tissue. Preferred methods of isolating mRNA encoding a protein of the present invention, along with other mRNA, from an mRNA source include poly U or poly dT chromatography. Other methods for RNA extraction, include an acid guanidinium thiocyanate procedure whereby adipose or skeletal muscle tissue total RNA and oligonucleotide primers are prepared for use in the isolation and cloning of the UCP-4 gene, as is known in the art.

Preferred methods of obtaining double-stranded cDNA from isolated mRNA include synthesizing a single-stranded cDNA on the mRNA template using a reverse transcriptase, degrading the RNA hybridized to the cDNA strand using a ribonuclease (RNase), and synthesizing a complementary DNA strand by using a DNA polymerase to give a double-stranded cDNA. Especially preferred methods of preparing cDNA include methods known to those skilled in the art, including; but not limited to, methods wherein total RNA is isolated from vertebrate brain, heart, pancreas, or skeletal muscle tissue is converted into single-stranded cDNA using Murine Leukemia Virus Reverse Transcriptase and RNase inhibitor, followed by a PCR procedure to amplify the target cDNA, yielding double-stranded cDNA.

cDNA encoding a protein of the present invention, along with the other cDNA if a library is constructed as above, are then ligated into cloning vectors. Cloning vectors include a DNA sequence which accommodates the cDNA. The vectors containing the amplified cDNA or cDNA library are introduced into host cells that can exist in a stable manner and provide an environment in which the cloning vector is replicated. Suitable cloning vectors include plasmids, bacteriophages, viruses and cosmids. Preferred cloning vectors include plasmids. Cloning vectors which are especially preferred in the isolation methods described herein for the preparation of RT-PCR products from total tissue RNA include the plasmid pAMP 1.

The construction of suitable cloning vectors containing cDNA and control sequences employs standard ligation and restriction techniques which are well known in the art. Isolated plasmids, DNA sequences or synthesized oligonucleotides are cleaved, tailored and relegated in the form desired. With respect to restriction techniques, site-specific cleavage of cDNA is performed by treating with suitable restriction enzyme under conditions which are generally understood in the art, and particulars of which are specified by the manufacturers of these commercially available restriction enzymes. See, erg., the product catalogs of New England Biolabs, Promega, and Stratagene Cloning Systems.

Cloning vectors containing the desired cDNA are introduced into host cells and cultured. Cloning vectors containing a cDNA library prepared as disclosed are introduced into host cells, the host cells are cultured, plated, and then probed with a hybridization probe to identify clones which contain the recombinant cDNA encoding a protein of the present invention. Preferred host cells include bacteria when plasmid cloning vectors are used. Especially preferred host cells include $E.$ $coli$ strains such as $E.$ $coli$ DH5 MCR competent cells.

Hybridization probes and primers are oligonucleotide sequences which are complementary to all or part of the cDNA molecule that is desired. They may be prepared using any suitable method, for example, the phosphotriester and phosphodiester methods, described respectively in Narang et al., Methods in Enzymology, 68:90 (1979) and Brown et al., Methods in Enzymology, 68:109 (1979), or automated embodiments thereof. In one such embodiment, diethylphosphoramidites are used as starting materials and may be synthesized as described by Beaucage et al., Tetrahedron Letters, 22:1859–1862 (1981). One method for synthesizing oligonucleotides on a modified solid support is described in U.S. Pat. No. 4,458,066. Probes differ from primers in that they are labeled with an enzyme, such as horseradish peroxidase, or with a radioactive atom, such as $^{32}P$, to facilitate their detection. A synthesized probe is radiolabeled by nick translation using $E.$ $coli$ DNA polymerase I or by end labeling using alkaline phosphatase and T4 bacteriophage polynucleotide kinase.

Useful hybridization probes and amplification primers include oligonucleotide sequences which are complementary to a stretch of the cDNA encoding a portion of the amino acid sequence of UCP-4, for example, a portion of the amino acid sequence shown in FIG. 1. Especially preferred as hybridization probes are oligonucleotide sequences encoding substantially all of the amino acid sequence of human UCP-4. Other appropriate probes for isolation of vertebrate UCP-4 genes will be apparent to those skilled in the art. Especially preferred as amplification primers are pairs of oligonucleotide sequences that flank substantially all of the DNA sequence encoding vertebrate UCP-4, for example, those encoding rat, mouse, or human UCP-4; A preferred cDNA molecule encoding a vertebrate protein of the present invention can be identified by screening or amplification methods through its ability to hybridize to these probes or primers.

Upon identification of the clone containing the desired cDNA, whether by an RT-PCR procedure or through cDNA library screening, for example, amplification may be used to produce large quantities of a gene encoding a protein of the present invention in the form of a recombinant cDNA molecule. Preferred methods of amplification include the use of the polymerase chain reaction (PCR). See, e.g., PCR Technology, W.H. Freeman and Company, New York (Edit. Erlich, H. A. 1992). PCR is an in vitro amplification method for the synthesis of specific DNA sequences. In PCR, two oligonucleotide primers that hybridize to opposite strands and flank the region of interest in the cDNA of the clone are used. A repetitive series of cycles involving cDNA denaturation into single strands, primer annealing to the single-stranded cDNA, and the extension of the annealed primers by DNA polymerase results in numbers of copies of cDNA, whose termini are defined by the 5' ends of the primers, approximately doubling at every cycle. Through PCR amplification, the coding domain and any additional primer encoded information such as restriction sites or translational signals (signal sequences, start and/or stop codons) of the recombinant cDNA molecule to be isolated is obtained. Preferred conditions for amplification of cDNA are found in manufacturer protocols, and may be accomplished manually or by automated thermocycling devices. An example of a cDNA prepared in this fashion is that having the nucleic acid sequence of FIG. 1.

The cDNA molecules of the present invention when isolated as described are used to obtain expression of the UCP-4s described and claimed herein. Generally, a recombinant cDNA molecule of the present invention is incorporated into an expression vector, this expression vector is introduced into an appropriate host cell, the host cell is cultured, and the expressed protein is isolated.

Expression vectors are DNA sequences that are required for the transcription of cloned copies of genes and translation of their mRNAs in an appropriate host. These vectors can express either procaryotic or eucaryotic genes in a variety of cells such as bacteria, yeast, mammalian, plant and insect cells. Proteins may also be expressed in a number of virus systems.

Suitably constructed expression vectors contain an origin of replication for autonomous replication in host cells, or are capable of integrating into the host cell chromosomes. Such vectors will also contain selective markers, a limited number of useful restriction enzyme sites, a high copy number, and strong promoters. Promoters are DNA sequences that direct RNA polymerase to bind to DNA and initiate RNA synthesis; strong promoters cause such initiation at high frequency; The preferred expression vectors of the present invention are operatively linked to a cDNA or recombinant cDNA of the present invention, i.e., the vectors are capable of directing both replication of the attached cDNA or recombinant cDNA molecule and expression of the protein encoded by the cDNA or recombinant cDNA molecule. Expression vectors may include, but are not limited to cloning vectors, modified cloning vectors and specifically designed plasmids or viruses. With each type of host cell certain expression vectors are preferred.

Procaryotes may be used and are presently preferred for expression of UCP-4. Suitable bacteria host cells include the various strains of *E. coli, Bacillus subtilis*, and various species of Pseudomonas. In these systems, plasmid vectors which contain replication sites and control sequences derived from species compatible with the host are used. Suitable vectors for *E. coli* are derivatives of pBR322, a plasmid derived from an *E. coli* species by Bolivar et al., *Gene*, 2:95 (1977). Common procaryotic control sequences, which are defined herein to include promoters for transcription, initiation, optionally with an operator, along with ribosome binding site sequences, include the beta-lactamase and lactose promoter (Chang et al., *Nature*, 198:1056 (1977)), the tryptophan promoter system (Goeddel et al., *Nucleic Acids Res.*, 8:4057 (1980)) and the lambda-derived $P_L$ promoter and N-gene ribosome binding site (Shimatake et al., *Nature*, 292:128 (1981)). However, any available promoter system compatible with procaryotes can be used. Preferred procaryote expression systems include *E. coli* and their expression vectors, such as *E. coli* strains W3110 and JM105, with suitable vectors. Especially preferred is the use of *E. coli* strain BL21(DE3), with suitable vectors.

Eucaryotes may be used for expression of the proteins of the present invention. Eucaryotes are usually represented by the yeast and mammalian cells. Suitable yeast host cells include *Saccharomyces cerevisiae* and *Pichia pastoris*. Suitable mammalian host cells include COS and CHO (Chinese Hamster Ovary) cells, NIH3T3, HEK293, and 3T3L1 cells. Expression vectors for the eucaryotes are comprised of promoters derived from appropriate eucaryotic genes. Suitable promoters for yeast cell expression vectors include promoters for synthesis of glycolytic enzymes, including those for the 3-phosphoglycerate kinase gene in *Saccharomyces cerevisiae* (Hitzman et al., *J. Biol. Chem.*, 255:2073 (1980)) and those for the metabolism of methanol such as the alcohol oxidase gene in *Pichia pastoris* (Stroman et al., U.S. Pat. Nos. 4,808,537 and 4,855,231). Other suitable promoters include those from the enolase gene (Holland et al., *J. Biol. Chem.*, 256:13 85 (1981)) or the Leu2 gene obtained from YEp13 (Broach et al., *Gene*, 8:121 (1978)).

Suitable promoters for mammalian cell expression vectors include the early and late promoters from SV40 (Fiers et al., *Nature*, 273:113 (1978)) or other viral promoters such as those derived from polyoma, adenovirus II, bovine papilloma virus or avian sarcoma viruses. Suitable viral and mammalian enhancers may also be incorporated into these expression vectors.

Suitable promoters for plant cell expression vectors include the nopaline synthesis promoter described by Depicker et al., *Mol. Appl. Gen.*, 1:561 (1978). Suitable promoters for insect cell expression vectors include modified versions of the system described by Smith et al., U.S. Pat. No. 4,475,051. The expression vector comprises a baculovirus polyhedrin promoter under whose control a cDNA molecule encoding a protein can be placed.

Another method of producing UCP-4 comprises the steps of culturing a transformed host cell containing a DNA sequence encoding a vertebrate UCP-4, preferably human UCP-4 and isolating the UCP-4 expressed by the transformed host cell. The host cell may be, for example, a yeast cell or other eukaryotic cell. Yeast cells are particularly preferred where the host cell will be used in an in vivo assay system for UCP-4 activity.

Expression of UCP-4 in a mammalian cell line where UCP-4 is not normally expressed, such as CHO, COS, NIH3T3, HEK293, or 3T3L1 cell lines is achieved using standard methods of stable transfection (Sambrook). A vector is constructed containing UCP-4 that allows inducible expression of UCP-4 in response to, for instance, the glucocorticoid analog, Dexamethasone or in response to removal of the antibiotic tetracycline. These inducible promoter systems are available commercially (Pharmacia and Clontech). Expression of UCP-4 in an inducible system allows the cells to grow normally in the absence of the predicted warming effects of ectopic expression of UCP-4 until the cells are at sufficient density to be used for the screening application, at which time UCP-4 expression may be readily induced.

Alternatively, UCP-1 and UCP-2 have successfully been expressed in yeast (Murdza-Inglis, D. L., et al. *JBC.* 260:11871–11875 (1991); Bathgate, B. et al. *Mol. Microbiol.* 6:363–37 (1992); Fleury, C., et al., *Nature Genetics*, 15:269–272 (1997)) Yeast vectors for the expression of UCP-4 in yeast preferably consist of an inducible promoter system such as the galactokinase gene enhancer/promoter, GAL1 (Mumberg, D., et al., *Nucleic Acids Res.* 22:5606–5768 (1994)). In this system, transcription is tightly repressed by addition to the growth medium of glucose but upon addition of galactose expression is induced to high levels. Deletions of this promoter and/or use of different plasmid types that direct replication to high or low copy numbers will allow expression levels of UCP-4 to be varied to achieve those optimal for both yeast survival and UCP-4 detection (Mumberg, D., et al., *Nucleic Acids Res.* 22:5767–5768 (1994)). The UCP-4 cDNA can also be modified so as to be optimal for expression in yeast cells: work with UCP-1 has shown that removal of the 5' and 3' untranslated regions of UCP-1 cDNA and modification of the UCP-1 sequence surrounding the methionine start codon to more closely resemble that normally found in yeast genes greatly improves expression levels in yeast (Murdza-Inglis, D. I., et al. *JBC* 260:11871–11875 (1991); Bathgate B., et al., *Mol. Microbiol.* 6:363–370 (1992)). These modifications can be readily achieved using PCR mutagenesis approaches such as are well known to those skilled in the art. In either case, yeast expression or mammalian expression, the UCP-4 gene can be additionally engineered, or not, by in frame addition, at the carboxy terminus of the UCP-4 cDNA, of an oligonucleotide sequence encoding a short peptide that is a characterized epitope, such as the commercially available FLAG system (Eastman Kodak Comp., New Haven, Conn.), or poly-histidine. This allows UCP-4 expression level and mitochondrial targeting to be monitored by the use of commercially available antibodies directed against the peptide epitope. The qualitative properties of yeast lines containing epitope tagged or wildtype UCP-4 will be compared to confirm that the peptide tag does not interfere with normal function. The use of such short sequence tags as markers for the detection of an expressed protein, as well as for purification of the expressed protein by affinity chromatography is known to those skilled in the art, and described in, for example, P.C.T. Application, US96/04909, published as WO-96-31526, Oct. 10, 1996, hereby incorporated by reference in its entirety.

The recombinant UCP-4-containing yeast cells or mammalian cell lines are expanded under non-inducing conditions and prior to screening are subjected to induction to allow UCP-4 production and insertion into mitochondrial membranes. Compounds (UCP-4 activators) may be identified by comparing their ability to stimulate respiration or metabolic activity of UCP-4-expressing cells, compared to control cells, which may be untransfected cells of the same genetic background. Alternatively, isolated mitochondrial preparations are used to screen for UCP-4 activators, either by measuring stimulation of respiration, or by measuring mitochondrial swelling in a suitable buffer system.

Where UCP-4 is to be isolated from the host cell, a prokaryotic cell such as E. coli may be used for UCP-4 expression. A number of recombinant production methods are described by contributors to Protein Purification—Micro to Macro, R. Burgess ed., Alan R. Liss, Inc., New York, 1987, and examples of periplasmic expression of recombinant proteins are given by H. Lee and P. Troota in *Purification and Analysis of Recombinant Proteins*, R. Seetharam and S. Sharma ed. Marcel Dekker, Inc., New York, 1991, p. 163–181. Provided herein are preferred methods for the periplasmic expression and purification of UCP-4, which provide increased protein yield and quality. These methods include the use of a T7 promoter vector construct transfected into E. coli BL21 (DE3) cells which are grown at about 25 to about 30 C in media containing a supplemental carbon source, preferably glucose, for enhanced expression. Preferred purification methods include the use of an osmotic shock protocol which incorporates one or more specific protease inhibitors, preferably Peflabloc SC, followed by the addition of BisTris-propane, or buffers of a similar nature, and separation using a cellulose-based anion exchange chromatography resin, preferably DE-52 resin. Further purification may be undertaken using high pressure liquid chromatography, preferably reversed phase high pressure liquid chromatography. Such methods are described in the below Examples.

Intracellular expression can be used to make proteins in *E. coli*, but the production process is complicated by the need to the dissolve the inclusion bodies using chaotropic agents and the difficulties inherent in refolding disulfide-bonded proteins, as discussed in *Protein Refolding*, G. Georgiou and E. Bernardez-Clark eds., (1991), American Chemical Society, Washington, DC. Also provided herein are preferred methods for the intracellular expression (into inclusion bodies) of recombinant UCP-4, and its subsequent solubilization, refolding and purification, which provide greatly increased protein yield in *E. coli*. In this method, certain naturally-occurring nucleotides within particular codons in the coding sequences for any of the mammalian UCP-4s, including human, rat and mouse (which are not part of the set of deleterious codons AGG/AGA, CUA, AUA, CGA, or CCC, described by J. Kane, *Curr. Opin. Biotechnol.* 6:494–500 (1995), are replaced.

Solubilization, refolding and purification of the recombinant proteins are accomplished by lysing the cells and washing inclusion bodies in an anionic buffer of approximately neutral pH, preferably 100 mM phosphate at a pH of about 6.5, dissolving the inclusion bodies in a buffer containing a chaotropic agent, such as urea in ammonium bicarbonate buffer, transferring the protein by dialysis or dilution into BisTris-propane or a similar buffer, and purifying the protein using a cellulose-based anion exchange chromatography resin, preferably DE-52 resin. Further purification may be undertaken using high pressure liquid chromatography, preferably reversed phase high pressure liquid chromatography.

The UCP-4s, derivatives, or analogs described herein may also be prepared through peptide synthesis.

While recombinant DNA methods of production are preferred, chemical synthesis, using a solid phase synthesis approach or a combination of both solid phase peptide synthesis and solution chemistries offers a further method of preparation of the UCP-4 products of the invention. Examples of solid phase peptide synthesis include that described by Merrifield, *J. Amer. Chem Soc.*, 85: 2149 (1964), or other equivalent methods known in the chemical arts, such as the method described by Houghten, *Proc. Natl. Acad. Sci.*, 82:5132 (1985).

Typically, an -N-carbamoyl protected amino acid and an amino acid attached to the growing peptide chain on a resin are coupled at room temperature in an inert solvent such as dimethylformamide, N-methylpyrrolidinone or methylene chloride in the presence of coupling agents such as dicyclohexylcarbodiimide and 1-hydroxybenzotriazole in the presence of a base such as diisopropylethylamine. The -N-carbamoyl protecting group is removed from the resulting peptide-resin using a reagent such as trifluoroacetic acid or piperidine, and the coupling reaction repeated with the next desired N-protected amino acid to be added to the peptide chain. Suitable N-protecting groups are well known in the art, with t-butyloxycarbonyl (tBoc) and fluorenylmethoxycarbonyl (Fmoc) being preferred herein.

The solvents, amino acid derivatives and 4-methylbenzhydryl-amine resin used in the peptide synthesizer may be purchased from Applied Biosystems Inc. (Foster City, Calif.), unless otherwise indicated. The sidechain protected amino acids may be purchased from Applied Biosystems, Inc. and include the following: Box-Arg(Mts), Fmoc-Arg(Pmc), Box-Thr(Bzl), Fmoc-Thr(t-Bu), Box-Ser (Bzl), Fmoc-Ser(t-Bu), Box-Tyr(BrZ), Fmoc-Tyr(t-Bu), Box-Lys(Cl-Z), Fmoc-Lys(Box), Box-Glu(Bzl), Fmoc-Glu (t-Bu), Fmoc-His(Trt), Fmoc-Asn(Trt), and Fmoc-Gln(Trt). Box-His(BOM) was purchased from Applied Biosystems, Inc. or Bachem Inc. (Torrance, Calif.). Anisole, methylsulfide, phenol, ethanedithiol, and thioanisole may be obtained from Aldrich Chemical Company (Milwaukee, Wis.). Air Products and Chemicals (Allentown, Pa.) supplied HF. Ethyl ether, acetic acid and methanol may be purchased from Fisher Scientific (Pittsburgh, Pa.).

Solid phase peptide synthesis is carried out with an automatic peptide synthesizer (Model 430A, Applied Biosystems Inc., Foster City, Calif.) using the NMP/HOBt (Option 1) system and tBoc or Fmoc chemistry (see, Applied Biosystems User's Manual for the ABI 430A Peptide Synthesizer, Version 1.3B Jul. 1, 1988, section 6, pp. 49–70, Applied Biosystems, Inc., Foster City, Calif.) with capping.

Box-peptide-resins are cleaved with HF (−5EC to 0EC, 1 hour). The peptide is extracted from the resin with alternating water and acetic acid, and the filtrates were lyophilized. The Fmoc-peptide resins are cleaved according to standard methods (*Introduction to Cleavage Techniques*, Applied Biosystems, Inc., 1990, pp. 6–12). Some peptide is also assembled using an Advanced Chem Tech Synthesizer (Model MPS 350, Louisville, Ky.). Peptides were purified by RP-HPLC (preparative and analytical) using a Waters Delta Prep 3000 system. A C4, C8 or C18 preparative column (10 F, 2.2×25 cm; Vydac, Hesperia, Calif.) is used to isolate peptides, and purity is determined using a C4, C8 or C 18 analytical column (5 F, 0.46×25 cm; Vydac). Solvents (A=0.1% TFA/water and B=0.1% TFA/$CH_3CN$) is delivered to the analytical column at a flowrate of 1.0 ml/min and to the preparative column at 15 ml/min. Amino acid analyses is performed on the Waters Pico Tag system and processed using the Maxima program. The peptides are hydrolyzed by vapor-phase acid hydrolysis (115EC, 20–24 h). Hydrolysates are derivatized and analyzed by standard methods (Cohen, S. A., Meys, M., and Tarrin, T. L. (1989), *The Pico Tag Method: A Manual of Advanced Techniques for Amino Acid Analysis*, pp. 11–52, Millipore Corporation, Milford, Mass.).

Fast atom bombardment analysis was carried out by M-Scan, Incorporated (West Chester, Pa.). Mass calibration is performed using cesium iodide or cesium iodide/glycerol. Plasma desorption ionization analysis using time of flight detection is carried out on an Applied Biosystems Bio-Ion 20 mass spectrometer.

Peptide compounds useful in the invention.may also be prepared using recombinant DNA techniques, using methods now known in the art. See, eg, Sambrook, et al., *Molecular Cloning: A Laboratory Manual*, 2d Ed., Cold Spring Harbor (1989).

UCP-4 analogs or derivatives are included within the methods of the present invention. UCP-4 analogs or derivatives are functional equivalents having similar amino acid sequence and retaining, to some extent, the thermogenic or other UCP-4-associated activity of UCP-4. By a "functional equivalent" is meant the derivative has an activity that can be substituted for one or more activities of UCP-4. Preferred functional equivalents retain all of the activities of UCP-4, however, the functional equivalent may have an activity that, when measured quantitatively, is stronger or weaker, as measured in UCP-4 functional assays. Preferred functional equivalents have activities that are within about 1% to about 10,000% of the activity of UCP-4, more preferably between about 10% to about 1000%, and more preferably within about 50% to about 500%. Derivatives have at least about 50% sequence similarity, preferably about 70%, more preferably about 90%, and even more preferably about 95% sequence similarity to UCP-4. "Sequence similarity" refers to "homology" observed between amino acid sequences in two different polypeptides, irrespective of polypeptide origin.

The ability of the derivative to retain some activity can be measured using techniques described herein. Derivatives include modifications occurring during or after translation, for example, by phosphorylation, glycosylation, crosslinking, acylation, proteolytic cleavage, linkage to an antibody molecule, membrane molecule or other ligand (see Ferguson et al., *Annu. Rev. Biochem.* 57:285–320, 1988).

Specific types of derivatives also include amino acid alterations such as deletions, substitutions, additions, and amino acid modifications. A "deletion" refers to the absence of one or more amino acid residue(s) in the related polypeptide. An "addition" refers to the presence of one or more amino acid residue(s) in the related polypeptide. Additions and deletions to a polypeptide may be at the amino terminus, the carboxy terminus, and/or internal. Amino acid "modification" refers to the alteration of a naturally occurring amino acid to produce a non-naturally occurring amino acid. A "substitution" refers to the replacement of one or more amino acid residue(s) by another amino acid residue(s) in the polypeptide. Derivatives can contain different combinations of alterations including more than one alteration and different types of alterations.

While the effect of an amino acid change varies depending upon factors such as phosphorylation, glycosylation, intrachain linkages, tertiary structure, and the role of the amino acid in the active site or a possible allosteric site, it is generally preferred that the substituted amino acid is from the same group as the amino acid being replaced. To some extent the following groups contain amino acids which are interchangeable: the basic amino acids lysine, arginine, and histidine; the acidic amino acids aspartic and glutamic acids; the neutral polar amino acids serine, threonine, cysteine, glutamine, asparagine and, to a lesser extent, methionine; the nonpolar aliphatic amino acids glycine, alanine, valine, isoleucine, and leucine (however, because of size, glycine and alanine are more closely related and valine, isoleucine and leucine are more closely related); and the aromatic amino acids phenylalanine, tryptophan, and tyrosine. In addition, although classified in different categories, alanine, glycine, and serine seem to be interchangeable to some extent, and cysteine additionally fits into this group, or may be classified with the polar neutral amino acids.

While proline is a nonpolar neutral amino acid, its replacement represents difficulties because of its effects on conformation. Thus, substitutions by or for proline are not preferred, except when the same or similar conformational results can be obtained. The conformation conferring properties of proline residues may be obtained if one or more of these is substituted by hydroxyproline (Hyp).

Examples of modified amino acids include the following: altered neutral nonpolar amino acids such as amino acids of the formula $H_2N(CH_2)_nCOOH$ where n is 2–6, sarcosine (Sar), t-butylalanine (t-BuAla), t-butylglycine (t-BuGly), N-methyl isoleucine (N-MeIle), and norleucine (Nleu); altered neutral aromatic amino acids such as phenylglycine; altered polar, but neutral amino acids such as citrulline (Cit) and methionine sulfoxide (MSO); altered neutral and nonpolar amino acids such as cyclohexyl alanine (Cha); altered acidic amino acids such as cysteic acid (Cya); and altered basic amino acids such as ornithine (Orn).

Preferred derivatives have one or more amino acid alteration(s) which do not significantly affect thermogenic or other UCP-4-associated activity of UCP-4. In regions of the UCP-4 peptide not necessary for UCP-4 activity, amino acids may be deleted, added or substituted with less risk of affecting activity. In regions required for UCP-4 activity, amino acid alterations are less preferred as there is a greater risk of affecting UCP-4 activity. Such alterations should be conservative alterations. For example, one or more amino acid residues within the sequence can be substituted by another amino acid of a similar polarity which acts as a functional equivalent.

Conserved regions tend to be more important for protein activity than non-conserved regions. Standard procedures can be used to determine the conserved and non-conserved regions important of receptor activity using in vitro mutagenesis techniques or deletion analyses and measuring receptor activity as described by the present disclosure.

Derivatives can be produced using standard chemical techniques and recombinant nucleic acid molecule techniques. Modifications to a specific polypeptide may be deliberate, as through site-directed mutagenesis and amino acid substitution during solid-phase synthesis, or may be accidental such as through mutations in hosts which produce the polypeptide. Polypeptides including derivatives can be obtained using standard techniques such as those described in Sambrook, et al., Molecular Cloning, Cold Spring Harbor Laboratory Press (1989).

UCP-4 agonists or UCP-4 analogs may also consist of UCP-4 fragments. Such fragments preferably have deletions of amino acids at either the amino- or carboxy-terminus. Fragments may be prepared by cleavage of the full length UCP-4 or by recombinant DNA-mediated or chemical synthesis of UCP-4 and UCP-4 derivatives.

Gene and oligonucleotide therapy methods of the present invention include the use of nucleic acid encoding functioning UCP-4 and the use of inhibitory oligonucleotides. Inhibitory oligonucleotides include antisense nucleic acids and ribozymes. Gene and oligonucleotide therapy can be performed ex vivo on cells which are then transplanted into a patient, or can be performed by direct administration of the nucleic acid or nucleic acid-protein complex into the patient.

Antisense oligonucleotides and ribozymes can be administered to a patient using different techniques such as by naked nucleic acid, nucleic acid compositions (for example, encapsulated by a liposome) and by retroviral vectors. Miller, *Nature* 357; 455–460, hereby incorporated by reference herein. Antisense oligonucleotides and ribozymes can also be introduced into a cell using nucleic acid encoding the antisense nucleic acid or ribozyme.

Gene therapy can be achieved by transferring a gene encoding UCP-4, or a compound that increases the expression of UCP-4, by, for example, inducing the UCP-4 promoter; into a patient in a manner allowing expression of UCP-4. Recombinant nucleic acid molecules encoding UCP-4 can be introduced into a cell in vivo or ex vivo. In vivo transfection techniques include the use of liposomes and retroviral vectors. Miller, *Nature* 357; 455–460, hereby incorporated by reference herein. Ex vivo transfection increases the number of available transfection techniques, but also adds additional complications due to removal and subsequent insertion of cells into a patient.

In preferred embodiments of the current invention, the nucleic acid utilized for gene therapy comprises a nucleic acid molecule which encodes the amino acid molecule of FIG. 1. More preferably the nucleic acid comprises the nucleic acid molecule of FIG. 1, or a portion thereof, and/or the oligonucleotides utilized for oligonucleotide therapy are targeted to a nucleic acid coding for UCP-4, more preferably a nucleic acid coding for the amino acid sequence of FIG. 1.

The present invention also contemplates antibodies and immunoassays useful for detecting the presence or amount of UCP-4 or a protein fragment of UCP-4. These antibodies have various uses such as being used as therapeutic agents to modulate UCP-4 activity; as diagnostic tools for determining the level of UCP-4 expression in a particular tissue and/or the UCP-4 functional integrity to diagnose a UCP-4 or thermogenic-related disease; and as research tools for studying UCP-4 synthesis, structure, and function. For example, antibodies targeted to UCP-4 are useful to elucidate which portion of UCP-4 a particular compound, such as a UCP-4 regulatory compound, binds.

The general methodology and steps of antibody assays are described by Greene, U.S. Pat. No. 4,376,110, entitled "Immunometric Assays Using Monoclonal Antibodies; *Antibodies, A Laboratory Manual*, Cold Spring Harbor Laboratory, Chapter 14 (1988);

Radioimmunoassay and related methods", A. E. Bolton and W. M. Hunter, Chapter 26 of *Handbook of Experimental Immunology*, Volume I, Immunochemistry, edited by D. M. Weir, Blackwell Scientific Publications, 1986; "Enzyme immunoassays: heterogeneous and homogeneous systems", Nakamura, et al., Chapter 27 of *Handbook of Experimental Immunology*, Volume 1, Immunochemistry, edited by D. M. Weir, Blackwell Scientific Publications, 1986; and *Current Protocols in Immunology*, Chapter 2, Section I, Edited by John E. Coligan, et al., (1991). In all such assays controls are preferably performed, which are designed to give positive and negative results. For example, the test may include a known UCP-4 peptide and a non-UCP-4 peptide negative control.

One such immunoassay is a sandwich immunoassay, and comprises the steps of (1) reacting an immobilized anti-UCP-4 antibody, preferably a monoclonal antibody, and a labeled anti-UCP-4 antibody, preferably a monoclonal antibody, which recognizes a different site from that recognized by the immobilized antibody, with a sample containing or suspected of containing UCP-4 so as to form a complex of immobilized antibody-UCP-4, and (2) detecting the presence or amount of UCP-4 by determining the presence or amount of label in the complex. In this process the reaction of the immobilized antibody and labeled antibody with the sample may be carried out either simultaneously or separately.

Antibodies that recognize UCP-4 can be prepared from hybridomas by the following method. UCP-4, peptides, or fragments thereof in an amount sufficient to promote formation of antibodies, are emulsified in an adjuvant such as Freund's complete adjuvant. The immunogen may be either crude or partially purified, and is administered to a mammal, such as mice, rats or rabbits, by intravenous, subcutaneous, intradermic, intramuscular, or intraperitoneal injection. In the preparation of polyclonal antibodies, after completion of the immunization protocol, sera are recovered from the immunized animals. In the preparation of monoclonal antibodies, after completion of the immunization protocol, animal spleens are harvested and myeloma cells having a suitable marker such as 8-azaguanine resistance can be used as parent cells which are then fused with the antibody-producing spleen cells to prepare hybridomas. Suitable media for the preparation of hybridomas according to the present invention include media such as Eagle's MEM, Dulbecco's modified medium, and RPMI-1640. Myeloma parent cells and spleen cells can be suitably fused at a ratio of approximately 1:4. Polyethylene glycol (PEG) can be used as a suitable fusing agent, typically at a concentration of about 35% for efficient fusion. Resulting cells may be selected by the HAT method (Littlefield, J. W., *Science* 145:709 (1964)). Screening of obtained hybridomas can be performed by conventional methods, including an immunoassay using culture supernatant of the hybridomas to identify a clone of hybridoma producing the objective immunoglobulin. The antibody-producing hybridoma obtained can then be cloned using known methods such as the limiting dilution method.

In order to produce, for example, the anti-UCP-4 monoclonal antibodies of the present invention, the hybridoma obtained above may be cultured either in vitro or in vivo. If the hybridoma is cultured in vitro, the hybridoma may be cultured in the above-mentioned media supplemented with fetal calf serum (FCS) for 3–5 days and monoclonal antibodies recovered from the culture supernatant. If the hybridoma is cultured in vivo, the hybridoma may be implanted in the abdominal cavity of a mammal, and after 1–3 weeks the ascites fluid collected to recover monoclonal antibodies therefrom. Much larger quantities of the monoclonal antibodies can efficiently be obtained using in vivo cultures rather than in vitro cultures and, thus, in vivo cultures are preferred. The monoclonal antibody obtained from the supernatant or ascites fluids can be purified by conventional methods such as ammonium sulfate-fractionation, Protein G-Sepharose column chromatography, or their combinations.

Antibodies, or the desired binding portions thereof including F(ab) and Fv fragments, along with antibody-based constructs such as single chain Fv's can also be generated using processes which involve cloning an immunoglobulin gene library in vivo. See, e.g., Huse et al., *Generation of a Large Combinatorial Library of the Immunoglobulin Repertoire in Phage Lambda*, (1989) *Science* 246:1275–1281. Using these methods, a vector system is constructed following a PCR amplification of messenger RNA isolated from spleen cells with oligonucleotides that incorporate restriction sites into the ends of the amplified product. Separate heavy chain and light chain libraries are constructed and may be randomly combined to coexpress these molecules together and screened for antigen binding. Single chain antibodies and fragments may also be prepared by this method.

Antibodies according to the present invention can suitably be immobilized on commercially available carriers for the antigen-antibody reaction including beads, balls, tubes, and plates made of glass or synthetic resin. Suitable synthetic resins include polystyrene and polyvinyl chloride. Anti-UCP-4 monoclonal antibodies are suitably absorbed onto the carrier by allowing them to stand at 2–8° C. overnight in 0.05M carbonate buffer, pH 9–10, preferably about pH 9.5. The immobilized anti-UCP-4 monoclonal antibody can be stored cold in the presence of preservatives such as sodium azide. Both monoclonal and polyclonal antibodies can be immobilized onto carriers using this method.

Labeled UCP-4 antibodies in accordance with the present invention can suitably be, prepared by labeling anti-UCP-4 antibodies with any substance commonly used for an immunoassay including radioisotopes, enzymes, and fluorescent substrates. Radioisotopes and enzymes are preferably used. When radioisotopes are used as labels, the antibody is preferably labeled with $^{125}$I using conventional methods such as the Chloramine T method (Hunter et al., *Nature* (1962) 194:495) and the Bolton-Hunter method. When enzymes are used as labels, the antibody is labeled with an enzyme such as horseradish peroxidase, -D-galactosidase, or alkaline phosphatase by conventional methods including the maleimide method and the Hingi method (Ishikawa et al, (1983) *J. Immunoassay* 4:1).

The activity of the label can be detected by conventional methods. If radioisotopes are used as labels, the activity of the label can be detected using an appropriate instrument such as a scintillation counter. If enzymes are used as labels, the activity of the label can be detected by measuring absorbance, fluorescence intensity, or luminescence intensity after reacting the enzyme with an appropriate substrate.

The present invention also provides a kit for assaying the amount of UCP-4, in either biological samples or samples of UCP-4. One example of such a kit comprises an immobilized anti-UCP-4 monoclonal antibody and a labeled anti-UCP-4 monoclonal antibody. When UCP-4s are assayed using this kit, UCP-4 becomes sandwiched between the immobilized monoclonal antibody and the labeled monoclonal antibody.

The different molecules of the present invention can be used to facilitate diagnosis of UCP-4-related diseases. Diagnosis can be carried out in vitro or in vivo. For example, the molecules of the present invention can be used to assay for defects in UCP-4 expression, structure, or activation.

Nucleic acid probes can be used to identify defects in UCP-4 occurring at the genetic level. For example, hybridization probes complementary to nucleic acid encoding UCP-4 can be used to clone UCP-4. The cloned UCP-4 can be inserted into a cell, such as an oocyte, and its responsiveness to a particular UCP-4-regulating compound determined. Another example of using hybridization assay probes to detect defects involves using the probes to detect mRNA levels or the presence of nucleic acid sequences associated with a particular disease. A decreased mRNA level would be consistent with a decreased amount of expressed UCP-4. Alternatively, defects in UCP-4 occurring at the genetic level may be determined by methods known to those skilled in the art, such as nucleic acid sequencing or PCR, which may reveal deletions or mutations in the UCP-4 nucleic acid molecule sequence.

The compounds useful in the present invention that regulate the activity of UCP-4 form salts with various inorganic and organic acids and bases. Such salts include salts prepared with organic and inorganic acids, for example, HCl, HBr, $H_2SO_4$, $H_3PO_4$, trifluoroacetic acid, acetic acid, formic acid, methanesulfonic acid, toluenesulfonic acid, maleic acid, fumaric acid and camphorsulfonic acid. Salts prepared with bases include ammonium salts, alkali metal salts, e.g. sodium and potassium salts, and alkali earth salts, e.g. calcium and magnesium salts. Acetate, hydrochloride, and trifluoroacetate salts are preferred. The salts may be formed by conventional means, as by reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

The compounds of the present invention are useful in view of their pharmacological properties. In particular, the compounds of the invention possess activity as agents to treat or prevent conditions or disorders related to thermogenesis such as, for example, obesity, malignant hyperthermia, and fever.

Compositions useful in the invention may conveniently be provided in the form of formulations suitable for parenteral (including intravenous, intramuscular and subcutaneous) or nasal or oral administration. In some cases, where the composition is administered to prevent or to treat obesity, it will be convenient to provide such compositions along with a food-intake-reducing, plasma glucose-lowering or plasma lipid-lowering agent, such as amylin, an amylin agonist, a leptin, an exendin, or an ob protein, in a single composition or solution for administration together. In other cases, it may be more advantageous to administer the additional agent separately from said compound. A suitable administration format may best be determined by a medical practitioner for each patient individually. Suitable pharmaceutically acceptable carriers and their formulation are described in standard formulation treatises, e.g., *Reming-* ton's *Pharmaceutical Sciences* by E. W. Martin. See also Wang, Y. J. and Hanson, M. A. "Parenteral Formulations of Proteins and Peptides: Stability and Stabilizers," *Journal of Parenteral Science and Technology*, Technical Report No. 10, Supp. 42:2S (1988).

Compounds useful in the invention can be provided as parenteral compositions for injection or infusion. They can, for example, be suspended in an inert oil, suitably a vegetable oil such as sesame, peanut, olive oil, or other acceptable carrier. Preferably, they are suspended in an aqueous carrier, for example, in an isotonic buffer solution at a pH of about 5.6 to 7.4. These compositions may be sterilized by conventional sterilization techniques, or may be sterile filtered. The compositions may contain pharmaceutically acceptable auxiliary substances as required to approximate physiological conditions, such as pH buffering agents. Useful buffers include for example, sodium acetate/acetic acid buffers. A form of repository or "depot" slow release preparation may be used so that therapeutically effective amounts of the preparation are delivered into the bloodstream over many hours or days following transdermal injection or delivery.

The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions.

The compositions can also be formulated as pharmaceutically acceptable salts (e.g., acid addition salts) and/or complexes thereof. Pharmaceutically acceptable salts are non-toxic salts at the concentration at which they are administered. The preparation of such salts can facilitate the pharmacological use by altering the physical-chemical characteristics of the composition without preventing the composition from exerting its physiological effect. Examples of useful alterations in physical properties include lowering the melting point to facilitate transmucosal administration and increasing the solubility to facilitate the administration of higher concentrations of the drug.

Pharmaceutically acceptable salts include acid addition salts such as those containing sulfate, hydrochloride, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethane sulfonic acid, benzenesulfonic acid, p-toluenesulfonic acid, cyclohexylsulfamic acid, and quinic acid. Such salts may be prepared by, for example, reacting the free acid or base forms of the product with one or more equivalents of the appropriate bas& or acid in a solvent or medium in which the salt is insoluble or in a solvent such as water which is then removed in vacuo or by freeze-drying or by exchanging the ions of an existing salt for another ion on a suitable ion exchange resin.

Carriers or excipients can also be used to facilitate administration of the compound. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents. The compositions or pharmaceutical composition can be administered by different routes including intravenously, intraperitoneal, subcutaneous, and intramuscular, orally, topically, or transmucosally.

If desired, solutions of the above compositions may be thickened with a thickening agent such as methyl cellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, eg., a Triton).

Compositions useful in the invention are prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

For use by the physician, the compositions will be provided in dosage unit form containing an amount of such UCP-4 activity-affecting composition. Those of skill in the art will recognize that the dosage will depend upon the purpose of administering said composition, and the severity of the disease or condition. For the treatment or prevention of obesity, for example, said composition may also comprise a food intake-reducing, plasma glucose-lowering or plasma lipid-lowering agent. In general, therapeutically effective amounts of such compositions are those that achieve the desired thermogenic, or obesity-decreasing effect, such as, for example, those that produce a significant reduction in weight when compared to a placebo-treated population. As will be recognized by those in the field, an effective amount of therapeutic agent will vary with many factors including the age and weight of the patient, the patient's physical condition, the blood sugar level and other factors.

The effective daily dose of such compounds will depend upon the purpose for which the compounds are administered. The exact dose to be administered is determined by the attending clinician and is dependent upon where the particular compound lies within the above quoted range, as well as upon the age, weight and condition of the individual. Administration should begin at the first sign of symptoms or shortly after diagnosis of obesity. Administration may be by injection, preferably subcutaneous or intramuscular. Orally active compounds may be taken orally, however dosages should be increased 5–10 fold.

The optimal formulation and mode of administration of compounds of the present application to a patient depend on factors known in the art such as the particular disease or condition, the desired effect, and the type of patient. While the compounds will typically be used to treat human subjects they may also be used to treat similar or identical diseases in other vertebrates such as other primates, farm animals such as swine, cattle and poultry, and sports animals and pets such as horses, dogs and cats.

To assist in understanding the present invention, the following Examples are included. The experiments relating to this invention should not, of course, be construed as specifically limiting the invention and such variations of the invention, now known or later developed, which would be within the purview of one skilled in the art are considered to fall within the scope of the invention as described herein and hereinafter claimed.

EXAMPLE 1

Characterization and Cloning of UCP-4

A search of the database of expressed sequence tags (dbEST) using "tblastn," one of the family of "BLAST"

sequence similarity algorithms (Altschul, S. F., et al. *J. Mol. Biol.* 215:403–410 (1990)), revealed a cDNA clone (I.D. 489443) which had some similarity to hUCP-3.

Clone ID 489443 (GenBank Accession No. AA054608), isolated from Soares NbHPU normal human pregnant uterus library, was obtained from the I.M.A.G.E. Consortium (Lennon, G. G., et al., *Genomics* 33:151–152 (1996)). The ~1.4 kilobase pair (kbp) insert was subcloned into the Not I and Eco RI sites of a modified pT7T3 vector (Pharmacia, Newark, N.J.) and sequenced.

DNA Sequencing

DNA was prepared using the ABI Prism Miniprep Kit (PE Applied Biosystems, Foster City, Calif.) and sequenced using the ABI Prism dRhodamine Terminator Cycle Sequencing Ready Reaction Kit (PE Applied Biosystems, Foster City, Calif.) following the manufacturer's protocol. Sequence reactions were thermocycled on the GeneAmp® PCR System 9700 and were run on the ABI Prism 377 automated sequencer (PE Applied Biosystems, Foster City, Calif.) following the manufacturer's protocol.

This sequencing of the cDNA insert of dbEST clone I.D. 489443 confirmed similarity with the amino terminal region of UCPs but also revealed an apparent nucleotide deletion relative to members of the UCP family. The consequence of this deletion is a frame shift and a deduced gene product both truncated and with no similarity to UCPs at its carboxyl terminus. Primers were designed and used to successfully amplify the complete coding region of this proposed transcript, herein referred to as UCP-4.

Oligonucleotide Synthesis

Oligonucleotides were synthesized (Life Technologies, Inc., Grand Island, N.Y.) for use as primers in polymerase chain reaction (PCR) amplifications. Primer A994 is a 23-mer from the 5'-untranslated region (UTR) sense strand: 5'-CUACUACUACUAGAGCAGCACCAGAAAAGTA CCAC-3' (corresponding to positions 1–23; FIG. 1). Primer A994 is an antisense strand 24 from the 3'UTR 5'-CAUCAUCAUCAUGGGCTGGGCTCACATATAAT TCAG-3'-(corresponding to positions 913–936; FIG. 1). Oligonucleotide A941 is a sense strand 27-mer: 5'-GAGCTACCAGTCTATGATATTACTAAG-3' (corresponding to positions 571–597; FIG. 1). Oligonucleotide A942 is an antisense 27-mer: 5'-AAGCCTCTTTAGCTGCTCGTATGTAAT-3' (corresponding to positions 874–900; FIG. 1).

Amplification of RNA

Reverse transcription of poly(A)$^+$ RNA to complementary DNA (cDNA) and subsequent amplification (RT-PCR) was accomplished using reagents from the GeneAmp RNA PCR kit (Perkin Elmer, Foster City, Calif.). 1 g of human brain poly(A)$^+$ RNA (Clontech, Palo Alto, Calif.) was reverse transcribed in a final 20 l volume containing 10 mM Tris-HCl, pH 8.3/50 mM KCl/5 mM MgCl$_2$/1 mM each dNTP/ 2.5 mM random hexamer primers/1 unit ml$^{-1}$ RNase inhibitor/2.5 units ml$^{-1}$ Moloney murine leukemia virus reverse transcriptase for 10 min at 22 C followed by 1 h at 42 C. The reaction was terminated by heating for 5 min at 99 C followed by chilling to 4 C. A 10 l aliquot of this cDNA pool was then PCR amplified by adjusting to a final 50 l volume containing 10 mM Tris-HCl, pH 8.3/50 mM KCl/1.5 mM MgCl$_2$/0.5 mM each upstream (A993) and downstream (A994) primer/0.2 mM each dNTP (contributed from the reverse transcription reaction) containing 2.5 units Ampli-Taq DNA Polymerase (Perkin Elmer). 40 cycles of denaturation for 30 sec at 95 C (2 min in the first cycle), annealing for 45 sec at 50 C, and extension for 1 min at 72 C were performed in a Perkin Elmer Cetus DNA thermal cycler and followed by a final extension at 72 C for 10 min. The PCR products were subsequently cloned into the pAMP vector (Life Technologies, Inc., Grand Island, N.Y.) following the manufacturer's UDG subcloning protocol.

The nucleotide sequence of UCP-4 amplified from human brain is presented in FIG. 1 (SEQ ID NO: 1). The deduced amino acid sequence of hUCP-4, as shown in FIG. 1 (SEQ. ID NO: 21) is comprised of 290 amino acid residues with a predicted molecular weight of 32449.22 daltons. The position of the initiation methionine residue was chosen based upon the similarity with the other UCP family members and a reasonable consensus site for translation initiation (Kozak, M., *J. Cell. Biol.* 108:229–241 (1989)).

Figure 2:
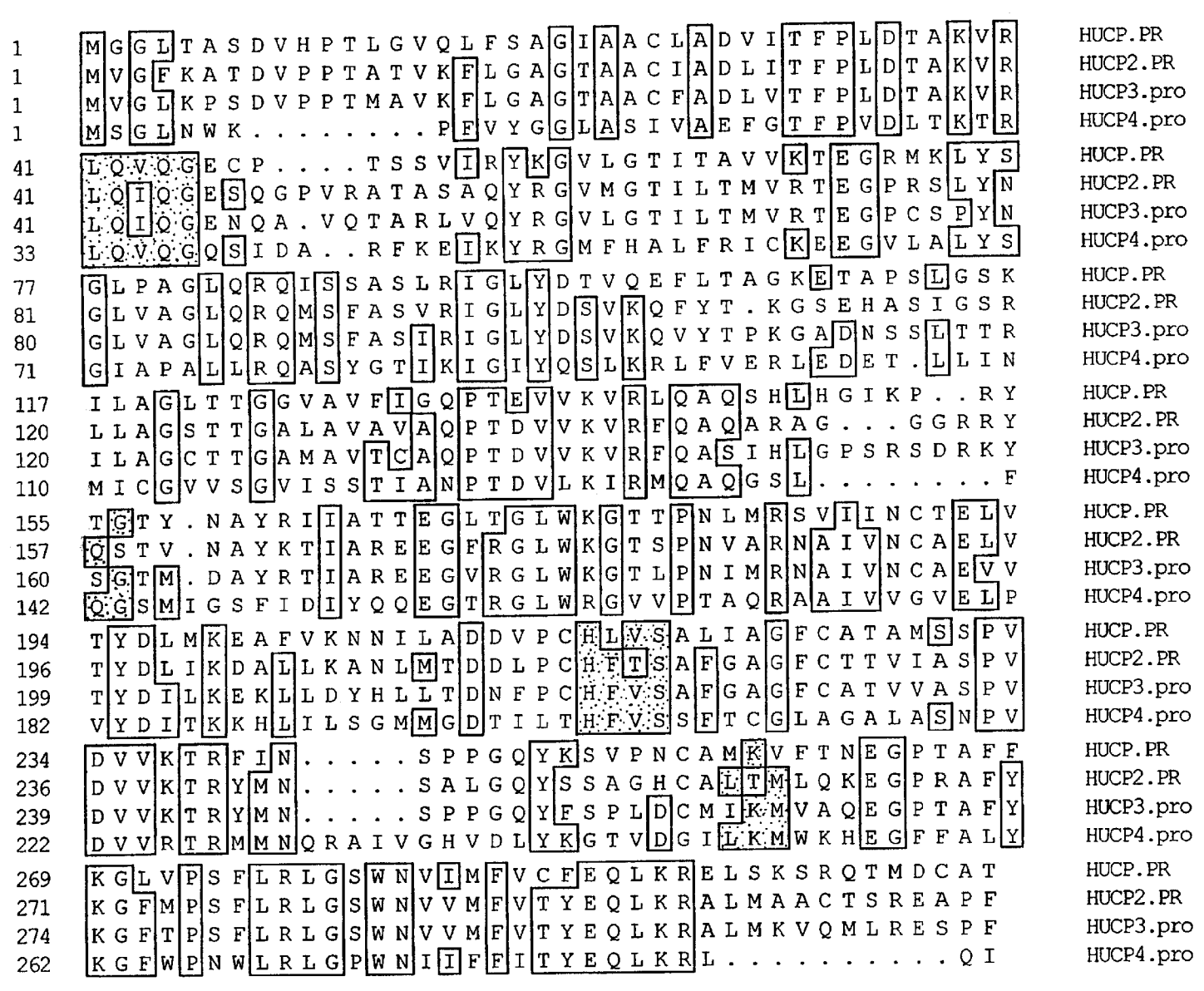

The UCP-4 sequence contains three consensus signature patterns (P-x-[DE]-x-[LIVAT]-[RK]-x-[LRH]-[LIVMFY]-[QGAIVM]) for inner mitochondrial membrane energy transfer proteins at positions 33–41, 136–144, and 234–242 (PROSITE database (Bairoch A., Bucher P. and Hofmann K., *Nucleic Acids Res.* 25:217–221 (1997)). Comparison of the amino acid sequence of hUCP-4 to those of hUCP-1, hUCP-2, and hUCP-3 is shown in FIG. 2. This alignment demonstrates 29.3%, 33.8% and 33.1% overall sequence similarity of UCP-4 with UCP-1, UCP-2 and UCP-3, respectively (Higgins, D. G. and Sharp, P. M., *CABIOS* 5:151–153 (1989)). The 57.1%–66.7% sequence similarity between UCP-4 and UCPs-1, 2, and 3 in the putative 6th transmembrane domain is particularly striking. In uncoupling proteins, the first 9 residues of this region (UCP-1 positions 262–270; FIG. 2) correspond to the putative nucleotide recognition element. Indeed, deletion of $Phe_{268}$-$Lys_{269}$-$Gly_{270}$ from UCP-1 reportedly resulted in an unregulated uncoupler, demonstrating that those residues are essential for the nucleotide inhibition of UCP-1 proton transport (Bouillaud, F., et al., *EMBO J.* 13:1990–1997 (1994)). The same authors also suggested that substituting Tyr (as found in UCP-4 as well as both UCP-2 and UCP-3) for $Phe_{268}$ may increase UCP-1 uncoupling activity.

$Arg_{277}$, conserved in all four members of the family, is directly involved in purine nucleotide regulation of UCP-1 transport function. Mutation of this residue reportedly resulted in the total abolition of GDP inhibition of UCP-1 proton transport (Murdza-Inglis, D. L., et al., *J. Biol. Chem.* 269:7435–7438 (1994)), although it is unclear if $Arg_{277}$ is directly involved in the GDP binding.

EXAMPLE 2

Tissue-Specific Expression of UCP-4

Probe preparation. A 330 base pair (bp) hUCP-4 DNA fragment, amplified from clone ID 489443, was used as template to prepare a radiolabeled probe. Briefly, 100 ng of clone ID 489443 plasmid DNA was amplified in a 50 ul reaction volume containing 10 mM Tris-HCl (pH8.3), 50 mM KCl, 1.5 mM MgCl$_2$, 0.5 uM of each primer (A941 and A942), 0.2 mM of each deoxy-NTP, and 2.5 U AmpliTaq® DNA polymerase (Perkin-Elmer). Twenty cycles of denaturation for 30 seconds at 94° C., annealing for 30 seconds at 65° C. and extension for 1 minute at 72° C. were followed by a final extension at 72° C. for 10 minutes. Amplification of the predicted product was confirmed by agarose gel electrophoresis of an aliquot of the reaction and subsequent visualization by ethidium bromide (EtBr) staining.

This 330 bp hUCP-4 gene-specific DNA fragment was radiolabeled to a specific activity of $5 \times 10^9$ cpm/ug essentially as described in Schowalter, D. B. and Sommer, S. S., *Anal. Biochem.* 177:90–94 (1989)). 1 ul of the above reaction was re-amplified in a 20 ul reaction containing 10 mM Tris-HCl (pH 8.3), 50 mM KCl, 1.5 mM MgCl$_2$, 0.5 uM each primer (A941 and A942), 0.2 mM dATP, 0.2 mM dGTP, 0.2 mM dTP, 2.5 mM [-$^{32}$P]dCTP (3000 Ci/mmole; 150 uCi; Amersham). The reaction was heated for 3 minutes at 94° C. at which time 1.25 U AmpliTaq® DNA polymerase (Perkin-Elmer) was added and followed by 30 cycles of denaturation for 1 minute at 94° C., annealing for 2 minutes at 55° C. and extension for 3 minutes at 72° C. A final 10 minute extension was performed at 72° C. prior to the removal of unincorporated nucleotides by spin filtration utilizing a ChromaSpin-100 DEPC H$_2$O column (Clontech, Palo Alto, Calif.) per the manufacturer's instructions.

Northern blot analysis. A human multiple tissue Northern blot (Clontech, Palo Alto, Calif.) containing 2 ug of poly (A)$^+$ RNA per lane from 8 different human tissues (heart; brain; placenta; lung; liver; skeletal muscle; kidney; pancreas) was prehybridized overnight at 65° C. in ExpressHyb (Clontech, Palo Alto, Calif.) hybridization solution containing 100 ug/ml heat-denatured, sheared salmon sperm DNA. The $^{32}$P-labeled human UCP-4 DNA probe, prepared as described above, was mixed with 30 ug of human C$_o$t-1 DNA (Life Technologies Inc., Grand Island, N.Y.) and 150 ug sheared salmon sperm DNA in 5×SSC (1×SSC=0.15 M NaCl and 0.015 M sodium citrate, pH 7.0), heat denatured for 5 min at 99 C, annealed for 30 min at 68 C, and added to 5 ml fresh ExpressHyb solution. Following hybridization at 65 C overnight, the blot was washed in 0.2×SSC/0.1% SDS at 50° C. and subsequently exposed to Kodak XAR film (Eastman Kodak, Rochester, N.Y.) with an intensifying screen at −80° C.

Northern blot analysis (FIG. 3) reveals a major hUCP-4 transcript of ~1.65 kb predominantly found in brain, heart, pancreas and skeletal muscle. The band on the autoradiogram is rather broad and close inspection suggests it might be a doublet representing two transcript species. UCP-4 transcripts are also detected at a lesser extent in kidney, placenta, liver and lung.

RNA dot blot analysis. A human RNA dot blot (TouchBlot; BioChain Institute, Inc., San Leandro, Calif.) containing 5 ug of total RNA from 48 human normal tissue samples was hybridized and washed under identical conditions as described above for the multiple-tissue Northern blot. The blot was then exposed to Kodak XAR film (Eastman Kodak) with an intensifying screen at −80° C.

Figure 4A:
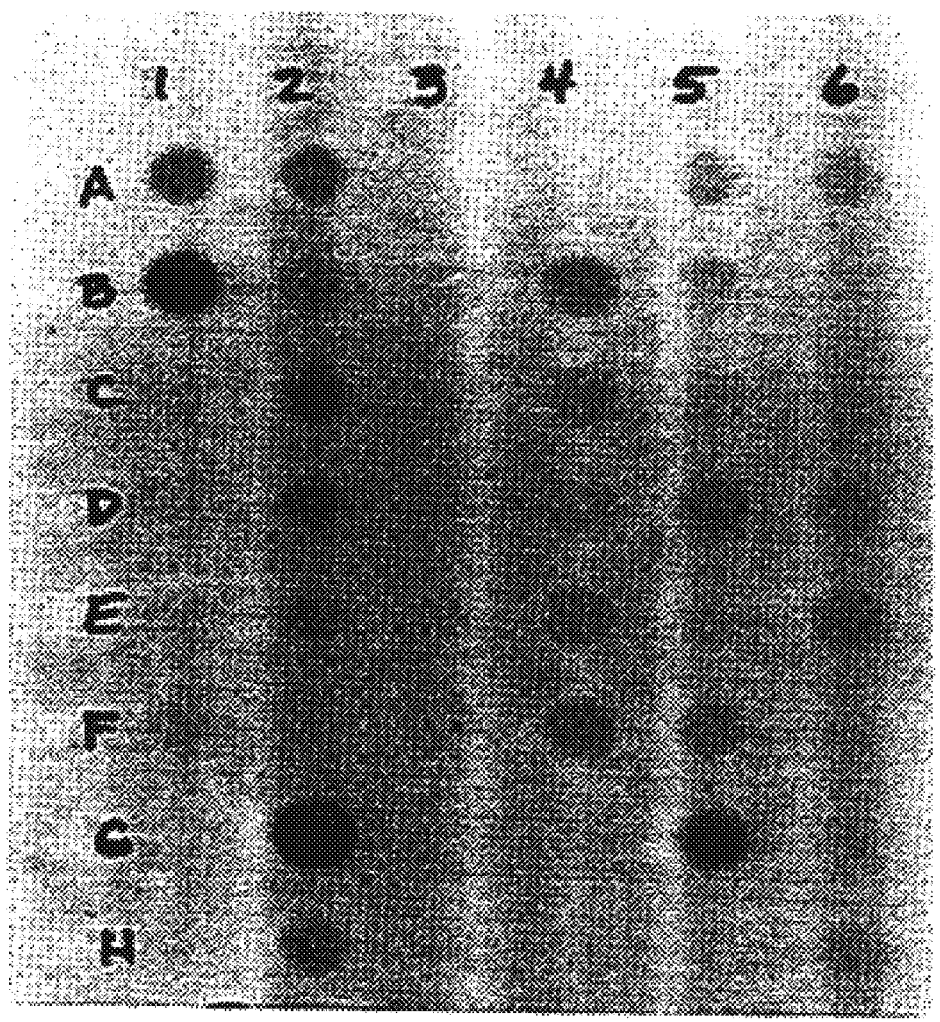

Total RNA dot blot analysis (FIG. 4) confirms the strong transcript signal in cerebellum and both right and left atriums as well signals from a variety of brain regions, ovary, spinal cord and other tissues, but absent from spleen and lymph node.

EXAMPLE 3

Regulation of UCP-4 Expression

UCP-1 expression is reported to be upregulated by cold acclimatization (via adrenergic stimulation of the brown fat depots) and by thyroid hormone (T$_3$) treatment (Rehnmark, S., et al., *J. Biol. Chem.* 265:16464–71 (1990); Ricquier, D., et al., *J. Biol. Chem.* 261:13905–10 (1986); Bianco, A. C., et al., *J. Biol. Chem.* 263:18168–75 (1988)). UCP-4 expression is tested to determine whether it would similarly be regulated, in vivo, by these treatments. These methods may also be used to determine whether UCP-4 is regulated by other environmental factors or compounds. The conservation of regulatory mechanisms between UCP-1 and UCP-4 may indicate that these proteins perform similar functions in the body in body temperature regulation and fuel efficiency modulation.

180–200 g male HSD rats are fed normal chow and kept in a 12 h light/dark cycle during the seven day treatment period, with 3–4 animals per group. A "control" group is maintained at 22 C (room temperature). A second group, "T3", is kept at 22 C but with 3.3 g/ml triiodothyronine in their drinking water (animals were drinking approx 30 ml/day=100 g/rat=500 g/kg) and a third group is maintained at 4 C ("cold acclimatized"). Following the treatment period animals are sacrificed by decapitation and tissues are harvested and immediately snap frozen in liquid N$_2$. Total RNA is isolated from skeletal muscle, heart, brain, and pancreas using the "Tri Reagent" following the manufacturer's instructions (Molecular Research Center, Cincinnati, Ohio). 20 g of RNA is loaded per lane onto 1% denaturing agarose gels and blotted to nitrocellulose membranes following standard protocols (See, e.g., Sambrook, et al., *Molecular Cloning: A Laboratory Manual*, 2d Ed., Cold Spring Harbor (1989)).

EXAMPLE 4

Screening for Compounds That Regulate UCP-4 Expression

To assay UCP-4 in the absence of any other UCP activity, yeast cells transformed with UCP-4 are preferred. Those skilled in the art will recognize that appropriate modifications to the assays may be easily made for the assay of UCP-4 activity in yeast cells, or in UCP-4 prepared from yeast cells. In addition, UCP-4-transformed cells, or cell-lines that express UCP-4, may be compared to non-UCP-4 transfected cells for activity in the presence or absence of test compounds in UCP-4-activity assays, for example, such as the assays described in this Example.

Preparation of Mitochondria

For immediate use in the respiration assay, the pellet is resuspended in 0.35 ml BSA-free isolation medium and held on ice until used. For use in the purine nucleotide binding assay, the pellet is resuspended in 3.0 ml BSA-free isolation medium, flash frozen on dry ice in 1.0 ml aliquots, and stored at −70 C until used.

Mitochondrial Membrane Purine Nucleotide Binding Assay

Fifty l of sample containing the test compound, or assay buffer (containing 250 mM sucrose, 20 mM HEPES, 2 mM EDTA, and 3 M rotenone at pH 7.0) and 50 l of 180 nM $^3$H-GDP are combined in the wells of a 96-well microtiter plate. Incubations are begun by the addition of 50 l suspension of mitochondria prepared from UCP-4-expressing cells containing 1.7 mg original wet weight. Nonspecific 3H-GDP binding is determined in the presence of 1 mM unlabeled GDP. After 60 minutes at room temperature, the incubation is stopped by filtration onto a Packard Unifilter using a Packard plate harvester. Filters are washed immediately before filtration with 4 ml phosphate buffered saline (PBS) and immediately after filtration with 12 ml PBS. Filters were dried overnight at room temperature, then counted on a Packard TopCount scintillation counter.

Mitochondria Respiration Assay

The oxygen sensor (YSI 5300) is calibrated, maintained, and operated as per manufacturer's instructions. In a 3 ml respiration chamber, 100 M laurate, 50 M guanine nucleotide diphosphate (GDP), appropriate concentrations of test sample or buffer, and 250 g mitochondria prepared from UCP-4-expressing cells are combined in 1 ml respiration medium containing 100 mM KCl and 10 mM TES (pH=7.0) at 25 C. After a 10 minute equilibration period, 16 mM succinate is added to stimulate increased mitochondrial respiration. Oxygen levels in each vessel were continuously recorded during the subsequent 10 to 12 minute period. The rate of oxygen consumption is determined for each sample as % decrease in nmoles $O_2$ per minute per mg protein, assuming 237 nmoles $O_2$/ml respiration medium.

Mitochondrial Swelling Assay

Mitochondria from cells expressing UCP-4 are isolated and reconstituted at 4 C in buffer containing 250 mM sucrose and 5mM TES at pH 7.2, at a concentration of approximately 5 mg protein/ml. To initiate swelling, mitochondria are diluted at least 10 fold (normally 30–40 fold into a buffer containing 100 mM KCl, 5mM TES and 4 M rotenone (to inhibit respiration) at pH 7.2. Mitochondria are incubated for 2 min at 23 C. Swelling of mitochondria is recorded by measuring the rate of change of optical density at 560 nm in a spectrophotometer (Molecular Devices SPECTRAmax 250). Addition of 0.5 M valinomycin (a potassium ionophore) to the mitochondria initiates rapid swelling and addition of GDP (50 M–1 mM) markedly inhibits valinomycin-induced swelling.

Whole Cell Respiration Assay

Cells expressing UCP-4 are counted and diluted to approximately 7.5×10 cells/ml to be used for oxygen consumption assays. Cells are maintained in an atmosphere of 95% $O_2$/5%$CO_2$ and gassed every 30 min. Oxygen consumption is measured as described in Example 3. Cells are diluted 1:10 in BSA-free Hanks BSS and 1 ml of cells added to the chamber (7.5×10$^4$ in 1 mg/ml BSA). Agents that affect cell respiration are added to the chamber once a stable rate of oxygen consumption is obtained. Oxygen consumption is expressed as nmoles/min/10$^6$ cells, based on a saturation of 950 nmol $O_2$/ml.

Whole Animal Respiration Assay

Plexi-glass animal holding-chambers with an approximate capacity of 1 liter are utilized to house the rats for indirect calorimetry. Each plexi-glass housing unit has an air intake port and an air exhaust port. Room air, at a flow rate of 0.5 l/min, is drawn past the animals using a multi-channel peristaltic pump (Cole-Parmer Instruments, Illinois). The exhaust from each animal chamber is sampled via a 16 channel port multiplexor for 10 seconds, at 1 minute intervals, for several hours to measure the Nitrogen, Oxygen and Carbon dioxide concentrations, using an MGA-3000, mass spectrometer gas analyzer (Airspec, England). During each sampling cycle, calibration gas (75% Nitrogen, 15% Oxygen, 5% Carbon dioxide, 5% Argon) is sampled to assure that the mass spectrometer is calibrated. These values are used to correct any drift in the $O_2$ and $CO_2$ measurement that may occur. Room air is also sampled during each sampling cycle, so that $O_2$ consumption and $CO_2$ production rate could be calculated by determining the difference between room air and the air flowing out from the animal chambers. The signals from the mass spectrometer are fed in to an IBM computer system to measure $O_2$ consumption and $CO_2$ production rates for each 10 second epoch.

Harlan Sprague-Dawley rats (250–300 gms) with chronic intravenous catheters are utilized for screening of compounds. After attaching a syringe, filled with test substance or vehicle, via a polyethylene tubing to the IV cannula, the rats are placed in the indirect calorimetry animal holding chamber and allowed to habituate for at least 45 minutes. Once the animals are calm, the experiment starts by collecting baseline measurements of $O_2$ consumption and $CO_2$ production. After 40 minutes of stable baseline, each animal is injected, via the IV cannula, with either vehicle or test compound, and the $O_2$ and $CO_2$ values monitored for 80 more minutes.

EXAMPLE 5

Cell Culture and Transfections

HEK-293 cells are transfected with a UCP-4 inducible expression vector. The day before transfection, HEK-293 cells are plated at 1.2×10$^7$ cells per T-162 cm$^2$ flasks (Costar) in maintenance medium: Minimum Essential Medium (Life-Technologies, Inc.) containing 10% fetal bovine serum (Irvine Scientific, Santa Ana, Calif.) and 2 mM L-glutamine (Life-Technologies, Inc.). The following day, the medium is aspirated and replaced with transfection mixture prepared per the manufacture's recommendations: 10 ml Opti-MEM containing 55 M 2-mercaptoethanol (Life-Technologies, Inc.), 150 g LipofectAMINE (Life-Technologies, Inc.), and 20 g DNA. After 5 hours, the transfection mixture is aspirated and replaced with HEK-293 maintenance medium containing 50 U/ml penicillin and 50 g/ml streptomycin (Life-Technologies, Inc.). For selection of stable transfectants, fresh medium containing 250 g/ml Zeocin™ (Invitrogen, San Diego, Calif.) is added 72 hours post-transfection. Cells are maintained at 37° C. in 5% $CO_2$–95% humidified air.

Various modifications of the invention in addition to those shown and described herein will become apparent to those skilled in the art from the foregoing description and fall within the scope of the following claims.

What is claimed is:

1. An isolated uncoupling protein 4 comprising the amino acid sequence of SEQ ID NO: 2.

2. The isolated uncoupling protein 4 of claim 1, wherein said isolated uncoupling protein 4 is isolated from a cell that comprises an endogenous nucleic acid molecule that encodes uncoupling protein 4.

3. The isolated uncoupling protein 4 of claim 1, wherein said uncoupling protein 4 is isolated from a cell that is transformed with a nucleic acid molecule that encodes uncoupling protein 4.

4. The isolated uncoupling protein 4 of claim 1, wherein said cell is selected from the group consisting of bacterial cells, insect cells, yeast cells, CHO cells, COS cells, NIH3T3 cells, HEK-293 cells, and 3T3L1 cells.

5. The isolated uncoupling protein 4 of claim 1, wherein said uncoupling protein 4 is chemically synthesized.

* * * * *